United States Patent
Bayever et al.

(10) Patent No.: US 9,492,442 B2
(45) Date of Patent: *Nov. 15, 2016

(54) METHODS FOR TREATING PANCREATIC CANCER USING COMBINATION THERAPIES COMPRISING LIPOSOMAL IRINOTECAN

(71) Applicant: MERRIMACK PHARMACEUTICALS, INC., Cambridge, MA (US)

(72) Inventors: Eliel Bayever, Cambridge, MA (US); Navreet Dhindsa, Boston, MA (US); Jonathan Basil Fitzgerald, Arlington, MA (US); Peter Laivins, Scituate, MA (US); Victor Moyo, Ringoes, NJ (US); Clet Niyikiza, Gulph Mills, PA (US); Jaeyeon Kim, Lexington, MA (US)

(73) Assignee: Merrimack Pharmaceuticals, Inc., Cambridge, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/851,111

(22) Filed: Sep. 11, 2015

(65) Prior Publication Data

US 2016/0074382 A1   Mar. 17, 2016

Related U.S. Application Data

(63) Continuation of application No. 14/406,776, filed as application No. PCT/US2013/045495 on Jun. 12, 2013.

(60) Provisional application No. 61/784,382, filed on Mar. 14, 2013, provisional application No. 61/659,211, filed on Jun. 13, 2012.

(51) Int. Cl.

| | |
|---|---|
| *A01N 43/00* | (2006.01) |
| *A61K 31/33* | (2006.01) |
| *A61K 38/00* | (2006.01) |
| *A61P 35/00* | (2006.01) |
| *A61K 31/4745* | (2006.01) |
| *A61K 31/573* | (2006.01) |
| *A61K 45/06* | (2006.01) |
| *A61K 31/513* | (2006.01) |
| *A61K 31/517* | (2006.01) |
| *A61K 9/00* | (2006.01) |
| *A61K 9/127* | (2006.01) |
| *A61K 31/519* | (2006.01) |

(52) U.S. Cl.
CPC ......... *A61K 31/4745* (2013.01); *A61K 9/0019* (2013.01); *A61K 9/127* (2013.01); *A61K 9/1271* (2013.01); *A61K 31/513* (2013.01); *A61K 31/517* (2013.01); *A61K 31/519* (2013.01); *A61K 31/573* (2013.01); *A61K 45/06* (2013.01)

(58) Field of Classification Search
None
See application file for complete search history.

(56) References Cited

U.S. PATENT DOCUMENTS

| | | | |
|---|---|---|---|
| 4,604,463 | A | 8/1986 | Miyasaka et al. |
| 5,013,556 | A | 5/1991 | Woodle et al. |
| 5,077,056 | A | 12/1991 | Bally et al. |
| 5,192,549 | A | 3/1993 | Barenolz et al. |
| 5,316,771 | A | 5/1994 | Barenholz et al. |
| 5,538,954 | A | 7/1996 | Koch et al. |
| 5,593,622 | A | 1/1997 | Yoshioka et al. |
| 5,676,971 | A | 10/1997 | Yoshioka et al. |
| 5,783,568 | A | 7/1998 | Schlessinger et al. |
| 5,785,987 | A | 7/1998 | Hope et al. |
| 5,846,458 | A | 12/1998 | Yoshioka et al. |
| 6,110,491 | A | 8/2000 | Kirpotin |
| 6,241,999 | B1 | 6/2001 | Ye et al. |
| 6,355,268 | B1 | 3/2002 | Slater et al. |
| 6,403,569 | B1 | 6/2002 | Achterrath |
| 6,465,008 | B1 | 10/2002 | Slater et al. |
| 6,720,001 | B2 | 4/2004 | Chen et al. |
| 6,794,370 | B2 | 9/2004 | Achterrath |
| 7,060,828 | B2 | 6/2006 | Madden et al. |
| 7,829,113 | B2 | 11/2010 | Okada et al. |
| 7,846,473 | B2 | 12/2010 | Yoshino et al. |

FOREIGN PATENT DOCUMENTS

| | | |
|---|---|---|
| WO | WOA1 9728156 | 8/1997 |
| WO | WOA1 03030684 | 4/2003 |

(Continued)

OTHER PUBLICATIONS

Kozuch et al., Irinotecan Combined with Gemcitabine, 5-Fluorouracil, Leucovorin, and Cisplatin (G-FLIP) is an Effective and Noncrossresistant Treatment for Chemotherapy Refractory Metastatic Pancreatic Cancer, 2001, The Oncologist, 6, pp. 488-495.*

Tsai et al., Nanovector-based therapies in advanced pancreatic cancer, 2011, Journal of Gastrointestinal Oncology, vol. 2, No. 3, pp. 185-194.*

The American Cancer Society, http://www.cancer.org/cancer/pancreaticcancer/detailguide/pancreatic-cancer-what-is-pancreatic-cancer.*

Chen, L., et al., "Expanded analyses of NAPOLI-1: Phase 3 study of MM-398 (nal-IRI), with or without 5-fluorouracil and leucovorin, versus 5-fluorouracil and leucovorin, in metastatic pancreatic cancer (mPAC) previously treated with gemcitabine-based therapy", Poster presented at the ASCO meeting of May 29-Jun. 2, 2015, Chicago, Illinois.

(Continued)

*Primary Examiner* — Kortney L Klinkel
*Assistant Examiner* — Tori M Strong
(74) *Attorney, Agent, or Firm* — Honigman Miller Schwartz and Cohn LLP; Noel E. Day; Cynthia M. Bott

(57) ABSTRACT

Provided are methods for treating pancreatic cancer in a patient by administering liposomal irinotecan (MM-398) alone or in combination with additional therapeutic agents. In one embodiment, the liposomal irinotecan (MM-398) is co-administered with 5-fluorouracil and leucovorin.

30 Claims, 7 Drawing Sheets

(56) References Cited

U.S. PATENT DOCUMENTS

| | | |
|---|---|---|
| 8,992,970 B2 | 3/2015 | Hong et al. |
| 2002/0102298 A1 | 8/2002 | Needham |
| 2002/0146450 A1 | 10/2002 | Slater et al. |
| 2002/0192275 A1 | 12/2002 | Zalipsky et al. |
| 2003/0138481 A1 | 7/2003 | Zadi |
| 2015/0182460 A1 | 7/2015 | Hong et al. |
| 2015/0182521 A1 | 7/2015 | Bayever et al. |
| 8,067,432 B2 | 11/2011 | Anderson et al. |
| 8,147,867 B2 | 4/2012 | Hong et al. |
| 8,329,213 B2 | 12/2012 | Hong et al. |
| 8,703,181 B2 | 4/2014 | Hong et al. |

(Continued)

FOREIGN PATENT DOCUMENTS

| | | |
|---|---|---|
| WO | WO 03030864 A1 | 4/2003 |
| WO | WO 2005107712 A1 | 11/2005 |

OTHER PUBLICATIONS

Gebbia, V. et al., "Irinotecan Plus Bolus/Infusional 5-Fluorouracil and Leucovorin in Patients With Pretreated Advanced Pancreatic Carcinoma: A Multicenter Experience of the Gruppo Oncologico Italia Meridionate", American Journal of Clinical Oncology, vol. 33, 5, Oct. 2010, 461-464.

Munstedt, et al. "Role of dexamethasone dosage in combination with 5-HT3 antagonists for prophylaxis of acute chemotherapy-induced nausea and vomiting" 1999, British Journal of Cancer, 79(3/4), pp. 637-639.

Onivyde [MM-398] label (Oct. 22, 2015). Retrieved from the Internet: http://www.accessdata.fda.gov/drugsatfda_docs/label/2015/207793lbl.pdf.

Wang-Gillam, A., et al., "Nanoliposomal irinotecan with flourouracil and folinic acid in metastatic pancreatic cancer after previous gemcitabine-based therapy (NAPOLI-1); a global, randomised, open-label, phase 3 trial", The Lancet, Published online Nov. 22, 2015; http://dx.doi.org/10.1016/S0140-6736(15)00986-1.

Camptosar label (labeling revision Dec. 12, 2014). Retrieved from the Internet: http://www.accessdata.fda.gov/drugsaftda_docs/label/2010/020571s031s032s033s036s037lbl.pdf.

Camptosar label (labeling revision May 14, 2010). Retrieved from the Internet: http://www.accessdata.fda.gov/drugsatfda_docs/label/2010/020571s031s032s033s036s037lbl.pdf.

Non-Final Rejection of U.S. Appl. No. 14/175,365 (U.S. Pat. No. 8,992,970), dated Jun. 26, 2014, and Notice of References, dated Jun. 26, 2014.

Final Rejection of U.S. Appl. No. 11/121,294 (U.S. Pat. No. 8,147,867), dated Nov. 23, 2011, and Notice of References, dated Nov. 23, 2011.

Katsu, T., et al., "Ion-Selective Electrode for Transmembrane pH Difference Measurements," Anal. Chem., vol. 73, 2001, pp. 1849-1854.

Chou, T., et al., "Effect of Composition on the Stability of Liposomal Irinotecan Prepared by a pH Gradient Method," Journal of Bioscience and Bioengineering, vol. 95 No. 4, 2003, pp. 405-408.

Author Unknown, "From Antinutrient to Phytonutrient: phytic acid gains respect," HighBeam Research, Environmental Nutrition, Apr. 1, 2004, 2 printed pages. URL: http://www.highbeam.com/doc/1G1-116341390.html/print (accessed Nov. 4, 2011).

Non-Final Rejection of U.S. Appl. No. 11/121,294 (U.S. Pat. No. 8,147,867), dated Apr. 13, 2011, and Notice of References, dated Apr. 13, 2011.

Miles, David, et al., "Combination Versus Sequential Single-Agent Therapy in Metastatic Breast Cancer," The Oncologist, 7(suppl 6), 2002, pp. 13-19.

Maddison, J.E., SW Page, D Church. "Small Animal Clinical Pharmacology," (2002), p. 474.

Nentwich, Phyllis F., "Intravenous Therapy," (1990), p. 310.

Hong, K., "Anti-HER2 Immunoliposomes for Targeted Drug Delivery," Annals New York Academy of Sciences, vol. 886, Dec. 1999, pp. 293-296.

Sadzuka, Yasuyuki, et al, "Effect of Liposomalization on the Antitumor Activity, Side-Effects, and Tissue Distribution of CPT-11," Cancer Letters 127 (1998), pp. 99-106.

Shimada, Shinya, et al., "Irinotecan Plus Low-Dose Cisplatin for Alpha-Fetoprotein-Producing Gastric Carcinoma with Multiple Liver Metastases: Report of Two Cases," Surgery Today (2002) 32, pp. 1075-1080.

Ahmad, Imran, et al., "Antibody-Targeted Delivery of Doxorubicin Entrapped in Sterically Stabilized Liposomes Can Eradicate Lung Cancer in Mice," Cancer Research 53, Apr. 1, 1993, pp. 1484-1488.

Lee, Chun Man, et al. "Novel Chondroitin Sulfate-binding Cationic Liposomes Loaded with Cisplatin Efficiently Suppress the Local Growth and Liver Metastasis of Tumor Cells in Vivo." Cancer Research 62, Aug. 1, 2002, pp. 4282-4288.

Yeh, Brian K., et al. "Structural Basis for Activation of Fibroblast Growth Factor Signaling by Sucrose Octasulfate," Molecular and Cellular Biology, vol. 22, No. 20, Oct. 2002, pp. 7184-7192.

Non-Final Rejection of U.S. Appl. No. 13/654,373 (U.S. Pat. No. 8,703,181), dated Aug. 12, 2013, and Notice of References, dated Aug. 12, 2013.

DOXIL label (labeling revision Jun. 10, 2008). Retrieved from the Internet: http://www.accessdata.fda.gov/drugsatfda_docs/label/2008/050718s033lbl.pdf.

Abraxane label (labeling revision Dec. 23, 2011). Retrieved from the Internet: http://www.accessdata.fda.gov/drugsatfda_docs/label/2011/021660s025s026s0291bl.pdf.

Dawidczyk, et al., "State-of-the-art in design rules for drug delivery platforms: Lessons learned from FDA-approved nanomedicines," Journal of Controlled Release 187 (2014), pp. 133-144.

CAS Registry Record for 23214-92-8 (doxorubicin), entered STN Nov. 16, 1984.

CAS Registry Record for 97682-44-5 (irinotecan), entered STN Aug. 18, 1985.

Gemzar label (labeling revision Feb. 4, 2011). Retrieved from the Internet: http://www.accessdata.fda.gov/drugsatfda_docs/label/2011/020509s069lbl.pdf.

Non-Final Rejection of U.S. Appl. No. 11/121,294 (U.S. Pat. No. 8,147,867), dated Dec. 6, 2010, and Notice of References, dated Dec. 6, 2010.

Non-Final Rejection of U.S. Appl. No. 11/121,294 (U.S. Pat. No. 8,147,867), dated Aug. 17, 2009, and Notice of References, dated Aug. 17, 2009.

Doxil label (labeling revision Apr. 15, 2015). Retrieved from the internet: http://www.accessdata.fda.gov/drugsatfda_docs/label/2015/050718s048lbl.pdf.

Abraxane label (labeling revision Jul. 21, 2015). Retrived from the Internet: http://www.accessdata.fda.gov/drugsaffda_docs/label/2015/021660s041lbl.pdf.

Gemzar label (labeling revision May 8, 2014). Retrieved from the Internet: http://www.accessdata.fda.gov/drugsaffda_docs/label/2014/020509s077lbl.pdf.

Drummond, Daryl. C., et al., "Development of a Highly Active Nanoliposomal Irinotecan Using a Novel Intraliposomal Stabilization Strategy," Cancer Research 2006; 66: (6). Mar. 15, 2006, pp. 3271-3277.

Rahma, O. E., et al. "Second-line treatment in advanced pancreatic cancer: a comprehensive analysis of published clinical trials," Annals of Oncology Advance Access published May 12, 2013, pp. 1-8.

Ko, A. H., et al. "A Multinational Phase II Study of PEP02 (MM-398), Liposome Irinotecan, for Patients with Gemcitabine-refractory Metastatic Pancreatic Cancer," Poster presented at the American Society of Clinical Oncology meeting, Jun. 3-Jun. 7, 2011, Chicago, Illinois.

Chen, L., et al. "Phase I study of liposome irinotecan (PEP02) in combination with weekly infusion of 5-FU/LV in advanced solid tumors," Journal of Clinical Oncology, 2010 ASCO Annual Meeting Abstracts, vol. 28, No. 15_suppl (May 20 Supplement) 2010: e13024.

(56) References Cited

OTHER PUBLICATIONS

"Study of PEP02 as a Second Line Therapy for Metastatic Pancreatic Cancer," Mar. 1, 2012. Retrieved from the Internet: ClinicalTrials.gov Archive.
"A multinational phase II study of PEP02 (liposome irinotecan) for patients with gemcitabine-refractory metastatic pancreatic cancer," J Clin Oncol, vol. 29 (2011) ASCO Annual Meeting.
Chen, L., et al., "Phase I Study of Liposome Encapsulated Irinotecan (PEP02) in Advanced Solid Tumor Patients," Poster presented at the ASCO meeting of May 30-Jun. 3, 2008, Chicago, Illinois.
Kim, J., et al., "Sustained Intratumoral activation of MM-398 results in superior activity over irinotecan demonstrated by using a systems pharmacology approach." Poster presented at the AACR Pancreatic Cancer Symposium, Jun. 18-21, 2012, New York, New York.
Ko, A-H, et al. "A multinational phase 2 study of nanoliposomal irinotecan sucrosafate (PEP02,MM-398) for patients with gemcitabine-refractory metastatic pancreatic cancer," British Journal of Cancer (2013), 109, pp. 920-925.
"A Randomized Phase II Study of PEP02 or Irinotecan in Combination With Leucovorin and 5-Flourouracil in Second Line Therapy of Metastatic Colorectal Cancer," Clinical Trials Identifier: NCT01375816, Jun. 16, 2011 version. Retrieved from the internet: ClinicalTrials.gov archive.
"A Phase II Study of PEP02 as a Second Line Therapy for Patients With Metastatic Pancreatic Cancer," Clincial Trials Identifier: NCT00813163, Mar. 1, 2012 version. Retrieved from the internet: ClinicalTrials.gov archive.
Makrilia, N., et al. "Treatment for Refractory Pancreatic Cancer," Highlights from the "2011 ASCO Gastrointestinal Cancers Symposium," San Francisco, CA, USA, Jan. 20-22, 2011, Journal of the Pancreas, vol. 12, No. 2—Mar. 2011 [ISSN 1590-8577], pp. 110-113.
Yi, Seong Yoon, et al., "Irinotecan monotherapy as second-line treatment in advanced pancreatic cancer," Cancer Chemother Pharmacol, (2009) 63, pp. 1141-1145.
Neuzillet, C., et al., "Folfiri regimen as second-/third-line chemotherapy in patients with advanced pancreatic adenocarcinoma refractory to gemcitabine and platinum salts: a retrospective series of 70 patients." 2011 Gastrointestinal Cancers Symposium, J Clin Oncol 29: 2011 (suppl 4; abstr 272), pp. 1-2.
Taieb, J., "FOLFIRI.3, a new regimen combining 5-fluorouracil, folinic acid and irinotecan, for advanced pancreatic cancer. results of an Association des Gastro-Enterologues Oncologues (Gastroenterologist Oncologist Association) multicenter phase II study," Annals of Oncology, vol. 19, Issue 3 (2007), 11 pages.
Chen, L., et al., "Phase I study of liposome encapsulated irinotecan (PEP02) in advanced solid tumor patients," Journal of Clinical Oncology, 2008 ASCO Annual Meeting Proceedings (Post-Meeting Edition), vol. 26, No. 15S (May 20 Supplement), 2008: 2565.
Ko, A. H., et al., "A multinational phase II study of PEP02 (liposome irinotecan) for patients with gemcitabine-refractory metastatic pancreatic cancer," J Clin Oncol 29: 2011 (suppl; abstr 4069) 2011 ASCO Annual Meeting.
U.S. Appl. No. 14/812,950, filed Jul. 29, 2015.
U.S. Appl. No. 14/844,500, filed Sep. 3, 2015.
U.S. Appl. No. 14/879,302, filed Oct. 9, 2015.
U.S. Appl. No. 14/879,358, filed Oct. 9, 2015.

Yoo, C., et al., "A randomised phased II study of modified FOLFIRI.3 vs. modified FOLFOX as second-line therapy in patients with gemcitabine-rafractory advanced pancreatic cancer," British Journal of Cancer (2009) 101, pp. 1658-1663.
Zaniboni, A., et al. "FOLFIRI as second-line chemotherapy for advanced pancreatic cancer: a GISCAD multicenter phase II study," Cancer Chemother Pharmacol (2012) 69, pp, 1641-1645.
Grant, et al., Dose-ranging evaluation of the substituted benzamide dazopride when used as an antiemetic in patients receiving anticancer chemotherapy, 1993, Cancer Chemotherapy and Pharmacology, 31, pp. 422-444.
Kozuch, et al., Irinotecan combined with Gemcitabine, 5-Fluorouracil, Leuvocorin, and Cisplatin (G-FLIP) is an effective and noncrossresistant treatment for chemotherapy refractory metastatic pancreatic cancer, 2001, The Oncologist, 6, pp. 488-495.
"Study of MM-398 Versus 5-Flurouracil and Leucovorin in Patients With Metastatic Pancreatic Cancer", Dec. 11, 2011 (Dec. 11, 2011), pp. 1-3, XP055075223. URL:http:///clinicaltrials.gov/archive/NCT01494506/2011__12__16.
"Study of MM-398 With or Without 5-Fluorouracil and Leucovorin, Versus 5-Fluorouracil and Leucovorin in Patients With Metastatic Pancreatic Cancer", Aug. 9, 2012, pp. 1-3, XP055075259, Retrieved from the Internet: URL:http://clinicaltrials.gov/archive/NCT01494506/2012__06__09.
Baker J. et al., Irinophore C, a Novel Nanoformulation of Irinotecan, Alters Tumors Vascular Function and Enhances the Distribution of 5-Fluorouracil and Doxorubicin, Clin Cancer Res 2008; 14(22), pp. 7260-7271.
Brixi-Benmansour, Hedia, et al, "Phase II study of first-line FOLFIRI for progressive metastatic well-differentiated pancreatic endocrine carcinoma", Digestive and Liver Disease, W.B. Saunders, GB, vol. 43, No. 11, Jul. 1, 2011, pp. 912-916.
Eisenhauer, E.A., et al., New response evaluation criteria in solid tumours: Revised RECIST guideline (version 1.1), European Journal of Cancer, 45, 2009, pp. 228-247.
Hoskins, J.M, et al., "UGT1A1*28 Genotype and Irinotecan-Induced Neutropenia: Dose Matters", JNCI Journal of the National Cancer Institute, vol. 99, No. 17, Sep. 5, 2007, pp. 1290-1295.
Infante, Jeffrey R ., et al, "Phase I and pharmacokinetics study of IHL-305.(PEGylated liposomal Irinotecan) in patients with advanced solid tumors", Cancer Chemotherapy and Pharmacology, Springer, Berlin, DE, vol. 70, No. 5, Sep. 2, 2012, pp. 699-705.
International Search Report and Written Opinion, PCT/US013/045495, dated Aug. 22, 2013, pp. 11.
Tsai, Chang-Sung, et al., "Nanovector-based therapies in advanced pancreatic cancer", Journal of Gastrointestinal Oncology, Sep. 1, 2011, pp. 185-194.
Verreault et al., Vascular normalization in orthotopic glioblastoma following intravenous treatment with lipid-based nanoparticulate formulations of irinotecan (Irinophore C™), doxorubicin (Caelyx®) or vincristine. BMC Cancer 2011, 11:124, pp. 1-18.
Waterhouse DN et al., Lipid-based nanoformulation of irinotecan: dual mechanism of action allows for combination chemo/angiogenic therapy. Nanomedicine (2011) 6(9), pp. 1645-1654.
Wilson WR and Hay MP., Targeting hypoxia in cancer therapy. Nat Rev Cancer. <http://www.ncbi.nlm.nih.gov/pubmed/21606941> Jun. 2011; 11(6), pp. 393-410.
International Preliminary Report on Patentability, PCT/US2013/045495, dated Dec. 16, 2014, pp. 1-8.

* cited by examiner

Accumulation of SN-38 in Tumors Following Treatment with Free Irinotecan or Nanoliposomal Irinotecan (MM-398).

Effect of MM-398 on Carbonic Anhydrase IX staining in the HT29 xenograft model.

FIG. 5

MM-398 PK in q3w (irinotecan, liposomes + free drug)

| Dose (mg/m²) & Study Parameters | PEP0203 | | | PEP0201 | | PEP0206 | | Campto Package insert | |
|---|---|---|---|---|---|---|---|---|---|
| | 60 (n=3) | 80 (n=6) | 100 (n=4) | 120 (n=2) | 120 (n=6) | 180 (n=4) | PEP02 120 (n=37) | Campto® 300 (n=27) | 125 mg/m² (N=64) | 340 mg/m² (N=6) |
| $C_{max}$ (μg/mL) | 29.93 (± 15.79) | 29.16 (± 5.24) | 44.06 (± 7.60) | 47.94 (± 16.29) | 79.4 (± 13.9) | 102 (± 17.6) | 68.8 (± 36.6) | 4.3 (± 1.2) | 1.66 (± 0.795) | 3.392 (± 0.874) |
| $t_{1/2}$ (h) | 24.02 (± 16.76) | 32.09 (± 19.26) | 46.11 (± 17.46) | 30.65 (± 5.32) | 29.5 (± 17.2) | 22.2 (± 11.5) | 21.2 (± 18.3) | 7.7 (± 4.4) | 5.9 (± 0.7) | 11.7 (± 1.0) |
| $AUC_{0-t}$ (μg·h/mL) | 1,047 (± 1,158) | 1,116 (± 618) | 2,193 (± 1,017) | 1,117 (± 368) | 2,635 (± 1,617) | 1,946 (± 1,022) | 1,051.5 (± 1,412.0) | 24.2 (± 7.7) | 10.2 (± 3.2) | 20.604 (± 6.027) |
| $AUC_{∞}$ (μg·h/mL) | 1,114 (± 1,278) | 1,211 (± 822) | 2,472 (± 1,251) | 1,281 (± 540) | 2,983 (± 1,940) | 1,963 (± 1,036) | 1,012.2 (± 1,501.9) | 25.2 (± 9.6) | | |
| Cl (L/h/m²) | 0.1249 (± 0.1053) | 0.1164 (± 0.0949) | 0.0547 (± 0.0359) | 0.1033 (± 0.0406) | 0.0531 (± 0.0367) | 0.119 (± 0.0783) | 0.191 (± 0.298) | 12.9 (± 4.7) | 13.3 (± 6.01) | 13.9 (± 4.0) |
| $V_d$ (L/m²) | 2.6 (± 1.44) | 2.93 (± 0.66) | 2.63 (± 0.48) | 3.16 (± 0.38) | 1.8 (± 0.771) | 1.97 (± 0.342) | 2.23 (± 0.69) | 98.5 (± 29.0) | 110 (± 68.5) | 234 (± 69.6) |

Note: AUC 0-T is defined as T = 24 hours for Camptosar package insert,
T = 49.5 hours for Camptosar in the PEP0206 study and
T = 169.5 hours for MM-398.

FIG. 6

Note: AUC 0-T is defined as T = 24 hours for Camptosar package insert,
T = 49.5 hours for Camptosar in the PEP0206 study and
T = 169.5 hours for MM-398.

MM-398 PK in q3w (SN-38)

| Dose (mg/m²) & Study / Parameters | PEP0203 60 (n=3) | PEP0203 80 (n=6) | PEP0203 100 (n=4) | PEP0203 120 (n=2) | PEP0201 120 (n=6) | PEP0201 180 (n=4) | PEP0206 PEP02 120 (n=37) | PEP0206 Camptoᵃ 300 (n=27) | Campto Package insert 125 mg/m² (n=64) | Campto Package insert 340 mg/m² (n=6) |
|---|---|---|---|---|---|---|---|---|---|---|
| C_max (ng/mL) | 7.02 (± 5.64) | 7.98 (± 4.29) | 7.39 (± 1.98) | 16.64 (± 9.39) | 9.2 (± 3.5) | 14.3 (± 6.16) | 8.79 (± 8.69) | 44.1 (± 28.2) | 26.3 (± 11.9) | 56.0 (± 28.2) |
| t₁/₂ (h) | 163.81 (± 172.3) | 53.76 (± 15.6) | 73.41 (± 18.3) | 26.23 (± 6.53) | 75.4 (± 43.89) | 58.0 (± 32.89) | 56.8 (± 114.6) | 22.8 (± 10.9) | 10.4 (± 3.1) | 21.0 (± 4.3) |
| AUC_0-t (ng·h/mL) | 367.40 (± 227) | 354.77 (± 149) | 551.40 (± 391.8) | 357.60 (± 155.7) | 710 (± 336) | 1,160 (± 969) | 467 (± 310) | 361 (± 125) | 229 (± 108) | 474 (± 245) |
| AUC_0-∞ (ng·h/mL) | 1,372.3 (± 1,119) | 592.16 (± 153) | 844.28 (± 444) | 474.00 (± 209) | 897 (± 680) | 1,420 (± 1,134) | 879 (± 1,426) | 440 (± 162) | — | — |

METHODS FOR TREATING PANCREATIC CANCER USING COMBINATION THERAPIES COMPRISING LIPOSOMAL IRINOTECAN

CROSS REFERENCE TO RELATED APPLICATIONS

This application is a continuation of U.S. application Ser. No. 14/406,776, filed Dec. 10, 2014, which is a 35 U.S.C. §371(c) United States National Phase of PCT/US2013/045495, filed Jun. 12, 2013, which claims the benefit of priority of U.S. Provisional Application No. 61/659,211, filed Jun. 13, 2012, and U.S. Provisional Application No. 61/784,382, filed Mar. 14, 2013, all of which are incorporated herein by reference in their entireties.

BACKGROUND

Despite improvements in cancer treatments, there remains a critical need to further improve therapies so as to prolong patients' lives while maintaining quality of life, particularly in the case of advanced cancers such as pancreatic cancers that often are, or become, resistant to current therapeutic modalities.

Incidence of pancreatic cancer has markedly increased during the past several decades. It now ranks as the fourth leading cause of cancer death in the United States. Pancreatic cancer's high mortality rate is due to a dearth of effective therapies and a complete absence of reliably durable therapies. Because of the location of the pancreas, pancreatic cancer is typically not diagnosed until a tumor has become large enough to produce systemic symptoms. This, coupled with the absence of good screening tools and a limited understanding of risk factors, results in patients usually having advanced disease, often advanced metastatic disease, at the time of diagnosis. Metastatic pancreatic cancer has a dismal prognosis and is almost uniformly fatal, with an overall survival rate of less than 4% at 5 years.

Chemotherapy with one or more of 5-fluorouracil (5-FU) and gemcitabine has been shown to prolong survival in pancreatic cancer. Combination therapies including folinic acid (leucovorin or levoleucovorin), 5-fluorouracil, and irinotecan (FOLFIRI), folinic acid, 5-fluorouracil, irinotecan and oxaliplatin (FOLFIRINOX), or, less commonly, a combination of folinic acid, 5-fluorouracil, and oxaliplatin (FOLFOX) are also used to treat some pancreatic cancers. Irinotecan is 7-ethyl-10-[4-(1-piperidino)-1-piperidino]carbonyloxycampothecin, IUPAC name (S)-4,11-diethyl-3,4,12,14-tetrahydro-4-hydroxy-3,14-dioxo1H-pyrano[3',4':6,7]-indolizino[1,2-b]quinolin-9-yl-[1,4'bipiperidine]-1'-carboxylate. Irinotecan is a member of the topoisomerase I inhibitor class of drugs and is a semi-synthetic and water soluble analog of the naturally-occurring alkaloid, camptothecin. Also known as CPT-11, irinotecan is currently marketed formulated as an aqueous solution as Camptosar® (irinotecan hydrochloride injection). Topoisomerase I inhibitors such as irinotecan work to arrest uncontrolled cell growth by inhibiting the unwinding of DNA and thereby preventing DNA replication.

The pharmacology of irinotecan is complex, with extensive metabolic conversions involved in the activation, inactivation, and elimination of the drug. Irinotecan is a prodrug that is converted by nonspecific carboxylesterases into a 100-1000 fold more active metabolite, SN-38. SN-38 is not recognized by P-glycoprotein, a drug transporter that plays an important role in acquired drug resistance by pumping certain drugs out of cells, so irinotecan is likely to be active in tumors resistant to other standard chemotherapies. In the body, SN-38 is cleared via glucuronidation, for which major pharmacogenetic variability has been described, and biliary excretion. These drug properties contribute to the marked heterogeneities in efficacy and toxicity observed clinically with irinotecan. Irinotecan hydrochloride injection is approved in the United States for treatment of metastatic colon or renal cancer and is also used to treat colorectal, gastric, lung, uterine cervical and ovarian cancers.

There are few approved treatment options for advanced or metastatic pancreatic cancers, particularly for those of exocrine origin. Single-agent gemcitabine is the current standard of care in first-line treatment of advanced and metastatic pancreatic adenocarcinoma. In clinical trials, single-agent gemcitabine has consistently demonstrated a median prolongation of survival of 5 to 6 months and a 1-year survival rate of about 20%. Single agent gemcitabine was also approved as second line treatment for patients previously treated with but no longer responsive to 5-fluorouracil, with a median overall prolongation of survival of 3.9 months.

Based upon what is known of the biology of pancreatic cancer, a variety of targeted agents have been evaluated, but only erlotinib, a protein tyrosine kinase inhibitor targeted to EGFR, has been approved for first-line use in advanced pancreatic cancer, and the approval is only for use in combination with gemcitabine. The co-administration of erlotinib with gemcitabine resulted in a statistically significant benefit in survival, and improvements in median survival (6.4 months vs. 5.9 months), and 1-year survival rate (24% vs. 17%) compared to gemcitabine alone. Clinical trials evaluating other targeted agents, including studies testing the antibodies bevacizumab and cetuximab, have been disappointingly negative. Thus, there is an urgent need for improvements in, and effective alternatives to, current therapies for pancreatic cancer. The disclosed invention addresses this need and provides other benefits.

SUMMARY

Provided are methods for treating pancreatic cancer in a patient (i.e., a human patient) comprising administering to the patient liposomal irinotecan (e.g., irinotecan sucrose octasulfate salt liposome injection, also referred to as MM-398) alone or in combination with 5-fluorouracil (5-FU) and leucovorin (together, 5-FU/LV), according to a particular clinical dosage regimen. Compositions adapted for use in such methods are also provided.

In one aspect, a method for treatment (e.g., effective treatment) of pancreatic cancer in a patient is provided, the method comprising: administering to the patient, and affective amount of liposomal irinotecan, wherein the method comprises at least one cycle, wherein the cycle is a period of 3 weeks, and wherein for each cycle the liposomal irinotecan is administered on day 1 of the cycle at a dose of 120 mg/m$^2$, except if the patient is homozygous for the UGT1A1*28 allele, wherein liposomal irinotecan is administered on day 1 of cycle 1 at a dose of 80 mg/m$^2$. In one embodiment, the dose of liposomal irinotecan administered to the patient homozygous for the UGT1A1*28 allele is increased after one cycle in increments of 20 mg/m$^2$, up to a maximum of 120 mg/m$^2$.

In another aspect, a method for treatment of pancreatic cancer in a patient is provided, the method comprising co-administering to the patient an effective amount each of liposomal irinotecan, 5-fluorouracil (5-FU), and leucovorin, wherein the method comprises at least one cycle of administration, wherein the cycle is a period of 2 weeks, and wherein for each cycle:

(a) liposomal irinotecan is administered to patients not homozygous for the UGT1A1*28 allele on day 1 of each cycle at a dose of 80 mg/m$^2$, and to patients homozygous for the UGT1A1*28 allele on day 1 of cycle 1 at a dose of 60 mg/m$^2$ and on day 1 of each subsequent cycle at a dose of ranging from 60 mg/m$^2$ to 80 mg/m$^2$ (e.g., 60 mg/m$^2$ or 70 mg/m$^2$ or 80 mg/m$^2$);

(b) 5-FU is administered at a dose of 2400 mg/m$^2$; and (c) leucovorin is administered at a dose of 200 mg/m$^2$ (l form, or levoleucovorin) or 400 mg/m$^2$ (l+d racemic form). In one embodiment, the dose of liposomal irinotecan administered to the patient homozygous for the UGT1A1*28 allele is increased after one cycle to 80 mg/m$^2$. In one embodiment, in each cycle, the liposomal irinotecan is administered prior to the leucovorin and the leucovorin is administered prior to the 5-FU.

In another embodiment, the liposomal irinotecan is administered intravenously over 90 minutes.

In another embodiment, the 5-FU is administered intravenously over 46 hours.

In another embodiment, leucovorin is administered intravenously over 30 minutes.

In another embodiment, prior to each administration of liposomal irinotecan, the patient is pre-medicated with dexamethasone and/or a 5-HT3 antagonist or another antiemetic.

In another embodiment, the pancreatic cancer is an exocrine pancreatic cancer selected from the group consisting of acinar cell carcinoma, adenocarcinoma, adenosquamous carcinoma, giant cell tumor, intraductal papillary-mucinous neoplasm (IPMN), mucinous cystadenocarcinoma, pancreatoblastoma, serous cystadenocarcinoma, and solid and pseudopapillary tumors.

In one embodiment, treating the patient results in a positive outcome, wherein the positive outcome is pathologic complete response (pCR), complete response (CR), partial response (PR) or stable disease (SD). In another embodiment, the combination therapy with liposomal irinotecan, 5-FU and leucovorin results in therapeutic synergy.

In another embodiment, the liposomal irinotecan is formulated as irinotecan sucrose octasulfate salt liposome injection (MM-398). Irinotecan sucrose octasulfate salt liposome injection may also be referred to as irinotecan HCl liposome injection because irinotecan HCl is the active pharmaceutical ingredient that is used to load irinotecan into liposomes containing triethylammonium sucrose octasulfate to prepare MM-398 liposomes. This nomenclature may be used even though the hydrochloride ion of the irinotecan HCl reacts with the triethylammonium ion of the triethylammonium sucrose octasulfate to yield triethylammonium chloride (triethylamine hydrochloride), leaving irinotecan sucrose octasulfate salt as the entrapped pharmaceutical agent within the MM-398 liposomes. In another aspect, kits for treating pancreatic cancer in a patient are provided, the kit comprising a dose of liposomal irinotecan and instructions for using liposomal irinotecan as described herein.

In another aspect, kits for treating pancreatic cancer in a patient are provided, the kit comprising a dose of each liposomal irinotecan, 5-fluorouracil (5-FU), and leucovorin, and instructions for using liposomal irinotecan, 5-FU, and leucovorin as described herein.

In one embodiment, the kit encompasses treating an exocrine pancreatic cancer selected from the group consisting of acinar cell carcinoma, adenocarcinoma, adenosquamous carcinoma, giant cell tumor, intraductal papillary-mucinous neoplasm (IPMN), mucinous cystadenocarcinoma, pancreatoblastoma, serous cystadenocarcinoma, and solid and pseudopapillary tumors.

In one embodiment, the liposomal irinotecan is liposomal irinotecan sucrose octasulfate salt injection (MM-398).

In another aspect, a formulation of liposomal irinotecan for co-administration with 5-fluorouracil (5-FU) and leucovorin in at least one cycle is provided, wherein the cycle is a period of 2 weeks, the formulation of irinotecan is a liposomal formulation of irinotecan, and wherein:

(a) liposomal irinotecan is administered to patients not homozygous for the UGT1A1*28 allele on day 1 of each cycle at a dose of 80 mg/m$^2$ and to patients homozygous for the UGT1A1*28 allele on day 1 of cycle 1 at a dose of 60 mg/m$^2$ and on day 1 of each subsequent cycle at a dose of 60 mg/m$^2$ or 80 mg/m$^2$;

(b) 5-FU is administered at a dose of 2400 mg/m$^2$; and (c) leucovorin is administered at a dose of 200 mg/m$^2$ (l form, or levoleucovorin) or 400 mg/m$^2$ (l+d racemic form).

In one embodiment, after cycle 1 the dose of liposomal irinotecan administered to the patient homozygous for the UGT1A1*28 allele is increased to 80 mg/m$^2$. In another embodiment, the liposomal irinotecan is administered intravenously over 90 minutes.

In another embodiment, the 5-FU is administered intravenously over 46 hours.

In another embodiment, leucovorin is administered intravenously over 30 minutes.

In another embodiment, prior to each administration of liposomal irinotecan, the patient is pre-medicated with dexamethasone and/or a 5-HT3 antagonist or another antiemetic.

In another embodiment, the pancreatic cancer is an exocrine pancreatic cancer selected from the group consisting of acinar cell carcinoma, adenocarcinoma, adenosquamous carcinoma, giant cell tumor, intraductal papillary-mucinous neoplasm (IPMN), mucinous cystadenocarcinoma, pancreatoblastoma, serous cystadenocarcinoma, and solid and pseudopapillary tumors.

In another embodiment, the liposomal formulation of irinotecan is irinotecan sucrose octasulfate salt liposome injection.

In another aspect is provided a method of improving chemotherapy outcomes by increasing tumor vascularity, the method comprising administering to a patient having a tumor an amount of irinotecan sucrose octasulfate salt liposome injection effective to increase tumor vascularity and concomitantly administering an effective amount of a chemotherapy agent other than irinotecan to the patient.

In another aspect is provided irinotecan sucrose octasulfate salt liposome injection for concomitant administration to a patient having a tumor of 1) an amount of irinotecan sucrose octasulfate salt liposome injection effective to increase tumor vascularity and 2) an effective amount of a chemotherapy agent other than irinotecan.

BRIEF DESCRIPTION OF THE DRAWINGS

FIG. 5 summarizes the pharmacokinetics of MM-398 in q3w (irinotecan, liposome+free drug).

FIG. 6 summarizes the pharmacokinetics of MM-398 in q3w.

DETAILED DESCRIPTION

I. Definitions

Figure 1:
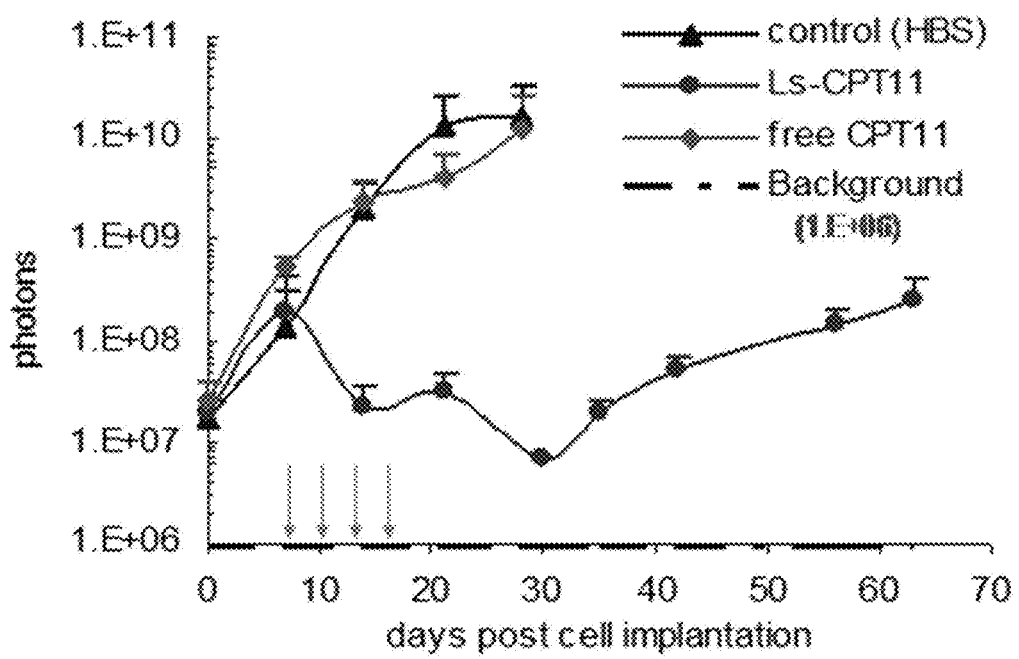
FIG. 1 is a graph showing the anti-tumor activity of MM-398 in an orthotopic pancreatic tumor model expressing luciferase (L3.6pl).

As used herein, the term "subject" or "patient" is a human cancer patient.

As used herein, "effective treatment" refers to treatment producing a beneficial effect, e.g., amelioration of at least one symptom of a disease or disorder. A beneficial effect can take the form of an improvement over baseline, i.e., an improvement over a measurement or observation made prior to initiation of therapy according to the method. A beneficial effect can also take the form of arresting, slowing, retarding, or stabilizing of a deleterious progression of a marker of a cancer. Effective treatment may refer to alleviation of at least one symptom of a cancer. Such effective treatment may, e.g., reduce patient pain, reduce the size and/or number of lesions, may reduce or prevent metastasis of a cancer tumor, and/or may slow growth of a cancer tumor.

The term "effective amount" refers to an amount of an agent that provides the desired biological, therapeutic, and/or prophylactic result. That result can be reduction, amelioration, palliation, lessening, delaying, and/or alleviation of one or more of the signs, symptoms, or causes of a disease, or any other desired alteration of a biological system. In reference to cancers, an effective amount comprises an amount sufficient to cause a tumor to shrink and/or to decrease the growth rate of the tumor (such as to suppress tumor growth) or to prevent or delay other unwanted cell proliferation. In some embodiments, an effective amount is an amount sufficient to delay tumor development. In some embodiments, an effective amount is an amount sufficient to prevent or delay tumor recurrence. An effective amount can be administered in one or more administrations. The effective amount of the drug or composition may: (i) reduce the number of cancer cells; (ii) reduce tumor size; (iii) inhibit, retard, slow to some extent and may stop cancer cell infiltration into peripheral organs; (iv) inhibit (i.e., slow to some extent and may stop) tumor metastasis; (v) inhibit tumor growth; (vi) prevent or delay occurrence and/or recurrence of tumor; and/or (vii) relieve to some extent one or more of the symptoms associated with the cancer.

The terms "combination therapy," "co-administration," "co-administered" or "concurrent administration" (or minor variations of these terms) include simultaneous administration of at least two therapeutic agents to a patient or their sequential administration within a time period during which the first administered therapeutic agent is still present in the patient when the second administered therapeutic agent is administered.

The term "monotherapy" refers to administering a single drug to treat a disease or disorder in the absence of co-administration of any other therapeutic agent that is being administered to treat the same disease or disorder.

"Dosage" refers to parameters for administering a drug in defined quantities per unit time (e.g., per hour, per day, per week, per month, etc.) to a patient. Such parameters include, e.g., the size of each dose. Such parameters also include the configuration of each dose, which may be administered as one or more units, e.g., taken at a single administration, e.g., orally (e.g., as one, two, three or more pills, capsules, etc.) or injected (e.g., as a bolus). Dosage sizes may also relate to doses that are administered continuously (e.g., as an intravenous infusion over a period of minutes or hours). Such parameters further include frequency of administration of separate doses, which frequency may change over time.

"Dose" refers to an amount of a drug given in a single administration.

As used herein, "cancer" refers to a condition characterized by abnormal, unregulated, malignant cell growth. In one embodiment, the cancer is an exocrine pancreatic cancer. In another embodiment, the exocrine pancreatic cancer selected from the group consisting of acinar cell carcinoma, adenocarcinoma, adenosquamous carcinoma, giant cell tumor, intraductal papillary-mucinous neoplasm (IPMN), mucinous cystadenocarcinoma, pancreatoblastoma, serous cystadenocarcinoma, and solid and pseudopapillary tumors.

The terms "resistant" and "refractory" refer to tumor cells that survive treatment with a therapeutic agent. Such cells may have responded to a therapeutic agent initially, but subsequently exhibited a reduction of responsiveness during treatment, or did not exhibit an adequate response to the therapeutic agent in that the cells continued to proliferate in the course of treatment with the agent.

II. Irinotecan Sucrose Sulfate Liposome Injection (MM-398; PEP02)

As provided herein, irinotecan is administered in a stable liposomal formulation as irinotecan sucrose sulfate liposome injection (otherwise termed "irinotecan sucrose octasulfate salt liposome injection" or "irinotecan sucrosofate liposome injection"), the formulation referred to herein as "MM-398" (also known as PEP02, see U.S. Pat. No. 8,147,867). MM-398 may be provided as a sterile, injectable parenteral liquid for intravenous injection. The required amount of MM-398 may be diluted, e.g., in 500 mL of 5% dextrose injection USP and infused over a 90 minute period.

An MM-398 liposome is a unilamellar lipid bilayer vesicle of approximately 80-140 nm in diameter that encapsulates an aqueous space which contains irinotecan complexed in a gelated or precipitated state as a salt with sucrose octasulfate. The lipid membrane of the liposome is composed of phosphatidylcholine, cholesterol, and a polyethyleneglycol-derivatized phosphatidyl-ethanolamine in the amount of approximately one polyethyleneglycol (PEG) molecule for 200 phospholipid molecules.

This stable liposomal formulation of irinotecan has several attributes that may provide an improved therapeutic index. The controlled and sustained release improves activity of this schedule-dependent drug by increasing duration of exposure of tumor tissue to drug, an attribute that allows it to be present in a higher proportion of cells during the S-phase of the cell cycle, when DNA unwinding is required as a preliminary step in the DNA replication process. The long circulating pharmacokinetics and high intravascular drug retention in the liposomes can promote an enhanced permeability and retention (EPR) effect. EPR allows for deposition of the liposomes at sites, such as malignant tumors, where the normal integrity of the vasculature (capillaries in particular) is compromised resulting in leakage out of the capillary lumen of particulates such as liposomes. EPR may thus promote site-specific drug delivery of liposomes to solid tumors. EPR of MM-398 may result in a subsequent depot effect, where liposomes accumulate in tumor associated macrophages (TAMs), which metabolize irinotecan, converting it locally to the substantially more cytotoxic SN-38. This local bioactivation is believed to result in reduced drug exposure at potential sites of toxicity and increased exposure at cancer cells within the tumor.

Pharmacogenetics of Irinotecan Glucuronidation

The enzyme produced by the UGT1A1 gene, UDP-glucuronosyltransferase 1, is responsible for bilirubin metabolism and also mediates SN-38 glucuronidation, which is the initial step in the predominant metabolic clearance pathway of this active metabolite of irinotecan. Besides its anti-tumor activity, SN-38 is also responsible for the severe toxicity sometimes associated with irinotecan therapy. Therefore, the glucuronidation of SN-38 to the inactive form, SN-38 glucuronide, is an important step in the modulation of irinotecan toxicity.

Mutational polymorphisms in the promoter of the UGT1A1 gene have been described in which there is a variable number of thymine adenine (ta) repeats. Promoters containing seven thymine adenine (ta) repeats (found in the UGT1A1*28 allele) have been found to be less active than the wild-type six repeats, resulting in reduced expression of UDP-glucuronosyltransferase 1. Patients who carry two deficient alleles of UGT1A1 exhibit reduced glucuronidation of SN-38. Some case reports have suggested that individuals who are homozygous for UGT1A1*28 alleles (referred to as having the UGT1A1 7/7 genotype, because both alleles are UGT1A1*28 alleles that contain 7 ta repeats, as opposed to the wild-type UGT1A1 6/6 genotype in which both alleles contain 6 ta repeats) and who have fluctuating elevation in serum bilirubin, (e.g., Gilbert's Syndrome patients), may be at greater risk of toxicity upon receiving standard doses of irinotecan. This suggests that there is a link between homozygosity of the UGT1A1*28 allele, bilirubin levels and irinotecan toxicity.

The metabolic transformation of MM-398 to SN-38 (e.g., in plasma) includes two critical steps: (1) the release of irinotecan from the liposome and (2) the conversion of free irinotecan to SN-38. While not intending to be limited by theory, it is believed that once irinotecan leaves the liposomes, it is catabolized by the same metabolic pathways as conventional (free) irinotecan. Therefore the genetic polymorphisms in humans predictive for the toxicity and efficacy of irinotecan and those of MM-398 can be considered similar. Nonetheless, due to the smaller tissue distribution, lower clearance, higher systemic exposure and longer elimination half-life of SN-38 of the MM-398 formulation compared to free irinotecan, the deficient genetic polymorphisms may show more association with severe adverse events and/or efficacy.

Patients with Reduced UGT1A1 Activity

Individuals who are homozygous for the UGT1A1*28 allele (UGT1A1 7/7 genotype) have been shown to be at increased risk for neutropenia following initiation of irinotecan treatment. According to the prescribing information for irinotecan (Camptosar®), in a study of 66 patients who received single-agent irinotecan (350 mg/m2 once every-3-weeks), the incidence of grade 4 neutropenia in patients homozygous for the UGT1A1*28 allele was as high as 50%, and in patients heterozygous for this allele (UGT1A1 6/7 genotype) the incidence was 12.5%. Importantly, no grade 4 neutropenia was observed in patients homozygous for the wild-type allele (UGT1A1 6/6 genotype). In other studies, a lower prevalence of life threatening neutropenia is described. For this reason, patients who are enrolled in the phase 3 study described in the Examples herein and are homozygous for the UGT1A1*28 allele (UGT1A1 7/7 genotype) will have MM-398 treatment initiated at a lower dose than patients with one (e.g., UGT1A1 6/7) or two (UGT1A1 6/6) wild-type alleles.

Additional genotypic modifiers of irinotecan metabolism Although the UGT1A1*28 allele is relatively common in Caucasians (estimates 10%), the prevalence is varied in other ethnic groups. Furthermore, additional UGT1A1 genotypes are found with higher prevalence for example in Asian populations and these could be important for the metabolism of irinotecan in these populations. For example, the UGT1A1*6 allele is more prevalent in Asians. This allele is not associated with a ta repeat, but with a Gly71Arg mutation that reduces enzyme activity. In previous and ongoing studies of MM-398, pharmacogenetic information has been collected on patients being enrolled. In a study referred to as the PEP0203 study, the relationship of genetic polymorphism of UGT1A family and of DPYD (dihydropyrimidine dehydrogenase, an enzyme associated with catabolism of 5-FU) with pharmacokinetic parameters of MM-398 and toxicity did not provide a clear correlation with the small sample size of subjects evaluated. However, it was observed that patients with UGT1A1*6/*28 combined polymorphism had higher dose-normalized AUCs of SN-38 and experienced DLT.

III. Fluorouracil (5-FU) and Leucovorin

5-Fluorouracil is a pyrimidine antagonist that interferes with nucleic acid biosynthesis. The deoxyribonucleotide of the drug inhibits thymidylate synthetase, thus inhibiting the formation of thymidylic acid from deoxyuridylic acid, thus interfering in the synthesis of DNA. It also interferes with RNA synthesis.

Leucovorin (also called folinic acid) acts as a biochemical cofactor for 1-carbon transfer reactions in the synthesis of purines and pyrimidines. Leucovorin does not require the enzyme dihydrofolate reductase (DHFR) for conversion to tetrahydrofolic acid. The effects of methotrexate and other DHFR-antagonists are inhibited by leucovorin. Leucovorin can potentiate the cytotoxic effects of fluorinated pyrimidines (i.e., fluorouracil and floxuridine). After 5-FU is activated within the cell, it is accompanied by a folate cofactor, and inhibits the enzyme thymidylate synthetase, thus inhibiting pyrimidine synthesis. Leucovorin increases the folate pool, thereby increasing the binding of folate cofactor and active 5-FU with thymidylate synthetase.

Leucovorin has dextro- and levo-isomers, only the latter one being pharmacologically useful. As such, the bioactive levo-isomer ("levoleucovorin") has also been approved by the FDA for treatment of cancer. The dosage of levoleucovorin is typically half that of the racemic mixture containing both dextro (d) and levo (l) isomers.

FU and leucovorin will be stored and handled according to the country specific package inserts.

IV. Administration

Liposomal irinotecan is administered intravenously, either alone or in combination with 5-fluorouracil (5-FU) and/or leucovorin. In one embodiment, liposomal irinotecan is administered prior to 5-FU and leucovorin. In another embodiment, leucovorin is administered prior to 5-FU. In another embodiment, liposomal irinotecan is administered intravenously over 90 minutes. In another embodiment, 5-FU is administered intravenously over 46 hours. In another embodiment, leucovorin is administered intravenously over 30 minutes. In various embodiments the liposomal irinotecan is MM-398.

V. Patient Populations

In one embodiment, a patient treated using the methods and compositions disclosed herein exhibits evidence of recurrent or persistent pancreatic cancer following primary chemotherapy.

In another embodiment, the patient has had and failed at least one prior platinum based chemotherapy regimen for management of primary or recurrent disease, e.g., a chemotherapy regimen comprising carboplatin, cisplatin, or another organoplatinum compound.

In an additional embodiment, the patient has failed prior treatment with gemcitabine or become resistant to gemcitabine.

In one embodiment a resistant or refractory tumor is one where the treatment-free interval following completion of a course of therapy for a patient having the tumor is less than 6 months (e.g., owing to recurrence of the cancer) or where there is tumor progression during the course of therapy.

In another embodiment, the pancreatic cancer of the patient undergoing treatment is advanced pancreatic cancer, which is a pancreatic tumor that exhibits either or both of distant metastasis or peripancreatic extension of the tumor.

The compositions and methods disclosed herein are useful for the treatment of all pancreatic cancers, including pancreatic cancers that are refractory or resistant to other anti-cancer treatments.

VI. Combination Therapy

In one embodiment, liposomal irinotecan is co-administered to patients having pancreatic cancer in combination with 5-fluorouracil (5-FU) and leucovorin, according to a particular clinical dosage regimen, such as those described herein. In one embodiment, the liposomal irinotecan is MM-398.

As used herein, adjunctive or combined administration (coadministration) includes simultaneous administration of the compounds in the same or different dosage form, or separate administration of the compounds (e.g., sequential administration). For example, liposomal irinotecan can be simultaneously administered with 5-FU and leucovorin. Alternatively, liposomal irinotecan can be administered in combination with 5-FU and leucovorin, wherein liposomal irinotecan, 5-FU and leucovorin are formulated for separate administration and are administered concurrently or sequentially. For example, liposomal irinotecan can be administered first followed by (e.g., immediately followed by) the administration of the 5-FU and leucovorin. Such concurrent or sequential administration preferably results in liposomal irinotecan, 5-FU, and leucovorin being simultaneously present in treated patients. In a particular embodiment, liposomal irinotecan is administered prior to 5-FU and leucovorin. In another particular embodiment, leucovorin is administered prior to 5-FU.

In another embodiment, liposomal irinotecan, 5-FU, and leucovorin are formulated for intravenous administration. In a particular embodiment, the patient is administered an effective amount each of liposomal irinotecan, 5-fluorouracil (5-FU), and leucovorin, wherein the treatment comprises at least one cycle, wherein the cycle is a period of 2 weeks, and wherein for each cycle: (a) liposomal irinotecan is administered on day 1 of the cycle at a dose of 80 mg/m$^2$, except if the patient is homozygous for the UGT1A1*28 allele, wherein liposomal irinotecan is administered on day 1 of cycle 1 at a dose of 60 mg/m$^2$; (b) 5-FU is administered at a dose of 2400 mg/m$^2$; and (c) leucovorin is administered at a dose of 200 mg/m$^2$ (l form) or 400 mg/m$^2$ (l+d racemic form) In a particular embodiment, the dose of liposomal irinotecan administered to the patient homozygous for the UGT1A1*28 allele is increased after one cycle to 80 mg/m$^2$.

In one embodiment, liposomal irinotecan may be initially administered at a high dose and may be lowered over time. In another embodiment, liposomal irinotecan is initially administered at a low dose and increased over time. In one embodiment, liposomal irinotecan is administered as a monotherapy.

In another embodiment, the dose of 5-FU is varied over time. For example, 5-FU may be initially administered at a high dose and may be lowered over time. In another embodiment, 5-FU is initially administered at a low dose and increased over time.

In another embodiment, the dose of leucovorin is varied over time. For example, leucovorin may be initially administered at a high dose and may be lowered over time. In another embodiment, leucovorin is initially administered at a low dose and increased over time.

VII. Treatment Protocols

Suitable treatment protocols include, for example, those wherein the patient is administered an effective amount of liposomal irinotecan, wherein the treatment comprises at least one cycle, wherein the cycle is a period of 3 weeks, and wherein for each cycle the liposomal irinotecan is administered on day 1 of the cycle at a dose of 120 mg/m$^2$, except if the patient is homozygous for the UGT1A1*28 allele, wherein liposomal irinotecan is administered on day 1 of cycle 1 at a dose of 80 mg/m$^2$. In one embodiment, the dose of liposomal irinotecan administered to the patient homozygous for the UGT1A1*28 allele is increased after one cycle in increments of 20 mg/m$^2$, up to a maximum of 120 mg/m$^2$.

In another embodiment, the treatment protocol includes administering to the patient an effective amount each of liposomal irinotecan, 5-fluorouracil (5-FU), and leucovorin, wherein the treatment comprises at least one cycle, wherein the cycle is a period of 2 weeks, and wherein for each cycle: (a) liposomal irinotecan is administered on day 1 of the cycle at a dose of 80 mg/m$^2$, except if the patient is homozygous for the UGT1A1*28 allele, wherein liposomal irinotecan is administered on day 1 of cycle 1 at a dose of 60 mg/m$^2$; (b) 5-FU is administered at a dose of 2400 mg/m$^2$; and (c) leucovorin is administered at a dose of 200 mg/m$^2$ (l form) or 400 mg/m$^2$ (l+d racemic form). In a particular embodiment, the dose of liposomal irinotecan administered to the patient homozygous for the UGT1A1*28 allele is increased after one cycle to 80 mg/m$^2$.

VIII. Outcomes

Provided herein are methods for treating pancreatic cancer in a patient comprising administering to the patient liposomal irinotecan (MM-398), alone or in combination with 5-fluorouracil (5-FU) and leucovorin, according to a particular clinical dosage regimen. Preferably, the combination therapy with liposomal irinotecan with 5-FU and leucovorin exhibits therapeutic synergy.

"Therapeutic synergy" refers to a phenomenon where treatment of patients with a combination of therapeutic agents manifests a therapeutically superior outcome to the outcome achieved by each individual constituent of the combination used at its optimum dose (T. H. Corbett et al., 1982, Cancer Treatment Reports, 66, 1187). In this context a therapeutically superior outcome is one in which the patients either a) exhibit fewer incidences of adverse events while receiving a therapeutic benefit that is equal to or greater than that where individual constituents of the combination are each administered as monotherapy at the same dose as in the combination, or b) do not exhibit dose-limiting toxicities while receiving a therapeutic benefit that is greater than that of treatment with each individual constituent of the combination when each constituent is administered in at the same doses in the combination(s) as is administered as individual components. In xenograft models, a combination, used at its maximum tolerated dose, in which each of the constituents will be present at a dose generally not exceeding its individual maximum tolerated dose, manifests therapeutic synergy when decrease in tumor growth achieved by administration of the combination is greater than the value of the decrease in tumor growth of the best constituent when the constituent is administered alone.

Thus, in combination, the components of such combinations have an additive or superadditive effect on suppressing pancreatic tumor growth, as compared to monotherapy with liposome-encapsulated irinotecan alone or treatment with the chemotherapeutic(s) in the absence of liposomal irinotecan therapy. By "additive" is meant a result that is greater in extent (e.g., in the degree of reduction of tumor mitotic index or of tumor growth or in the degree of tumor shrinkage or the frequency and/or duration of symptom-free or symptom-reduced periods) than the best separate result achieved by monotherapy with each individual component, while "superadditive" is used to indicate a result that exceeds in extent the sum of such separate results. In one embodiment, the additive effect is measured as slowing or stopping of pancreatic tumor growth. The additive effect can also be measured as, e.g., reduction in size of a pancreatic tumor, reduction of tumor mitotic index, reduction in number of metastatic lesions over time, increase in overall response rate, or increase in median or overall survival.

One non-limiting example of a measure by which effectiveness of a therapeutic treatment can be quantified is by calculating the log 10 cell kill, which is determined according to the following equation:

$$\log 10 \text{ cell kill} = T\ C(\text{days})/3.32 \times Td$$

in which T C represents the delay in growth of the cells, which is the average time, in days, for the tumors of the treated group (T) and the tumors of the control group (C) to have reached a predetermined value (1 g, or 10 mL, for example), and Td represents the time, in days necessary for the volume of the tumor to double in the control animals. When applying this measure, a product is considered to be active if log 10 cell kill is greater than or equal to 0.7 and a product is considered to be very active if log 10 cell kill is greater than 2.8. Using this measure, a combination, used at its own maximum tolerated dose, in which each of the constituents is present at a dose generally less than or equal to its maximum tolerated dose, exhibits therapeutic synergy when the log 10 cell kill is greater than the value of the log 10 cell kill of the best constituent when it is administered alone. In an exemplary case, the log 10 cell kill of the combination exceeds the value of the log 10 cell kill of the best constituent of the combination by at least 0.1 log cell kill, at least 0.5 log cell kill, or at least 1.0 log cell kill.

Responses to therapy may include:

Pathologic complete response (pCR): absence of invasive cancer in the breast and lymph nodes following primary systemic treatment.

Complete Response (CR): Disappearance of all target lesions. Any pathological lymph nodes (whether target or non-target) which has reduction in short axis to <10 mm;

Partial Response (PR): At least a 30% decrease in the sum of dimensions of target lesions, taking as reference the baseline sum diameters;

Stable Disease (SD): Neither sufficient shrinkage to qualify for partial response, nor sufficient increase to qualify for progressive disease, taking as reference the smallest sum diameters while on study; or Meanwhile, non-CR/Non-PD denotes a persistence of one or more non-target lesion(s) and/or maintenance of tumor marker level above the normal limits.

Progressive Disease (PD) denotes at least a 20% increase in the sum of dimensions of target lesions, taking as reference the smallest sum on study (this includes the baseline sum if that is the smallest on study). In addition to the relative increase of 20%, the sum must also demonstrate an absolute increase of 5 mm. The appearance of one or more new lesions is also considered progression.

In exemplary outcomes, patients treated according to the methods disclosed herein may experience improvement in at least one sign of pancreatic cancer.

In one embodiment the patient so treated exhibits pCR, CR, PR, or SD. In another embodiment, the patient so treated experiences tumor shrinkage and/or decrease in growth rate, i.e., suppression of tumor growth. In another embodiment, unwanted cell proliferation is reduced or inhibited. In yet another embodiment, one or more of the following can occur: the number of cancer cells can be reduced; tumor size can be reduced; cancer cell infiltration into peripheral organs can be inhibited, retarded, slowed, or stopped; tumor metastasis can be slowed or inhibited; tumor growth can be inhibited; recurrence of tumor can be prevented or delayed; one or more of the symptoms associated with cancer can be relieved to some extent.

In other embodiments, such improvement is measured by a reduction in the quantity and/or size of measurable tumor lesions. Measurable lesions are defined as those that can be accurately measured in at least one dimension (longest diameter is to be recorded) as ≥10 mm by CT scan (CT scan slice thickness no greater than 5 mm), 10 mm caliper measurement by clinical exam or >20 mm by chest X-ray. The size of non-target lesions, e.g., pathological lymph nodes can also be measured for improvement. In one embodiment, lesions can be measured on chest x-rays or CT or MRI films.

In other embodiments, cytology or histology can be used to evaluate responsiveness to a therapy. The cytological confirmation of the neoplastic origin of any effusion that appears or worsens during treatment when the measurable tumor has met criteria for response or stable disease can be considered to differentiate between response or stable disease (an effusion may be a side effect of the treatment) and progressive disease.

In some embodiments, administration of effective amounts of liposomal irinotecan, 5-FU and leucovorin according to any of the methods provided herein produce at least one therapeutic effect selected from the group consisting of reduction in size of a breast tumor, reduction in number of metastatic lesions appearing over time, complete remission, partial remission, stable disease, increase in overall response rate, or a pathologic complete response. In some embodiments, the provided methods of treatment produce a comparable clinical benefit rate (CBR=CR+PR+SD≥6 months) better than that achieved by the same combinations of anti-cancer agents administered without concomitant MM-398 administration. In other embodiments, the improvement of clinical benefit rate is about 20% 20%, 30%, 40%, 50%, 60%, 70%, 80% or more compared to the same combinations of anti-cancer agents administered without concomitant MM-398 administration.

The following examples are illustrative and should not be construed as limiting the scope of this disclosure in any way;

many variations and equivalents will become apparent to those skilled in the art upon reading the present disclosure.

EXAMPLES

Example 1

Activity of MM-398 in an Orthotopic Pancreas Tumor Model Expressing Luciferase (L3.6pl)

The anti-tumor activity of MM-398 was assessed in an orthotopic pancreatic cancer model (L3.6pl), a highly hypoxic preclinical tumor model. Approximately $2.5 \times 10^{-5}$ L3.6pl pancreatic tumor cells were implanted by direct injection into the pancreas. The bioluminescence images (BLI) were followed over time for tumor burden detection/quantitation. MM-398 and free irinotecan were dosed at a dose of 20 mg/kg/dose weekly for three weeks. As shown in FIG. 1, MM-398 (liposomal CPT11) had significant anti-tumor activity, as compared to a control (HBS) and free CPT11.

Example 2

Accumulation of SN-38 in Tumors Following Treatment with Free Irinotecan or Liposomal Irinotecan (MM-398)

It was hypothesized that the anti-tumor activity observed in the orthotopic pancreatic cancer model is due to the effect of macrophages in converting irinotecan to the more active SN-38 locally. To test this hypothesis, human colon cancer cells (HT-29) were injected subcutaneously into SCID mice, 40 mg/kg of free irinotecan or MM-398 was injected intravenously when the tumors reached 1000 mm³ in size. Tumor-bearing mice were sacrificed at different time points, tumors from both groups were extracted and the concentrations of SN-38 were measured.

Figure 2:
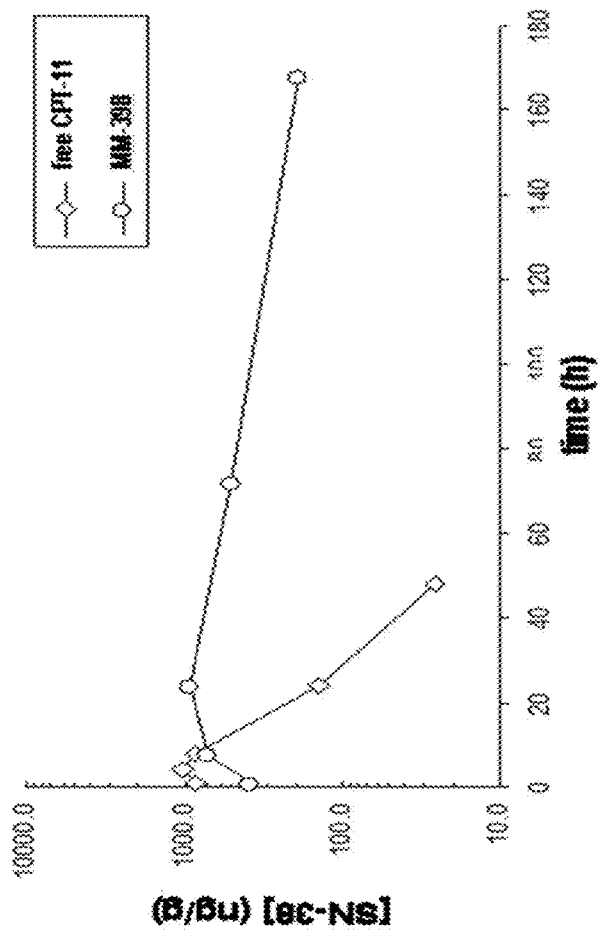
FIG. 2 is a graph showing accumulation of SN-38 in tumors following treatment with free irinotecan or liposomal irinotecan (MM-398).

As shown in FIG. 2, there was a 20-fold increase in the tumor $AUC_{SN-38}$ for MM-398 as compared to free irinotecan. The long duration of exposure allows for prolonged exposure of the slow proliferating cancer cells to the active metabolite as they progress through the cell cycle. In addition, this activity was also hypothesized to result from a reduction in intra-tumoral hypoxia, and the subsequent downstream effects on angiogenesis, metastasis, and the immunosuppressive environment in tumors.

Example 3

Effect of MM-398 on Carbonic Anhydrase IX Staining in a HT29 Xenograft Model

To test whether MM-398 reduces markers of hypoxia, experiments were conducted in a human colon cancer cell (HT-29) model. Specifically, HT-29 cells were injected subcutaneously into nude mice, on day 13 either PBS control or 1.25, 2.5, 5, 10 or 20 mg/kg MM-398 was injected intravenously. MM-398 was dosed once a week for 4 weeks at the indicated doses. Tumors from both groups (n=5) were extracted 24 hours after the last dose. Frozen tumor sections were used for immunohistochemical staining of Carbonic Anhydrase IX (CAIX). Quantification of CAIX staining was performed using Definiens® (Definiens AG, Munich) software.

Figure 3:
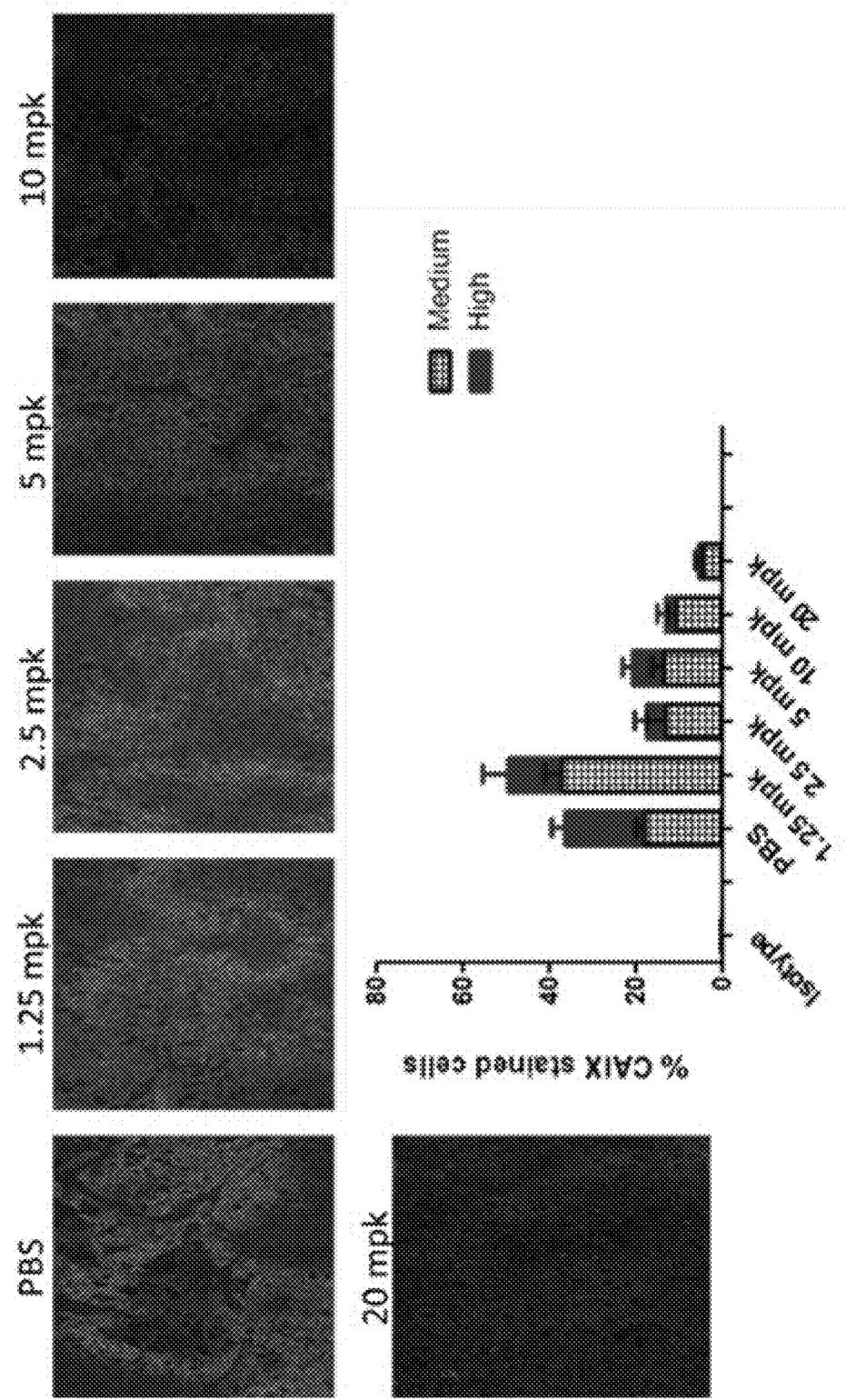
FIG. 3 is a graph showing the effect of MM-398 on Carbonic Anhydrase IX Staining in a HT29 Xenograft Model.

As shown in FIG. 3, MM-398 reduced markers of hypoxia. Specifically, the graphs in FIG. 3 show the percentage of cells that stained with medium (middle third) or high (top third) intensity for CAIX. Representative samples from each group are shown as well as the group average (mean+/-stdev). MM-398 treatment modifies the tumor microenvironment by decreasing the percentage of both medium and high CAIX positive cells in a dose-dependent manner. As hypoxia is a hallmark of resistant and aggressive disease, a reduction in hypoxia is expected to make tumor cells more sensitive to chemotherapies.

Example 4

MM-398 Increases Perfusion of Hoechst Stain

Figure 4:
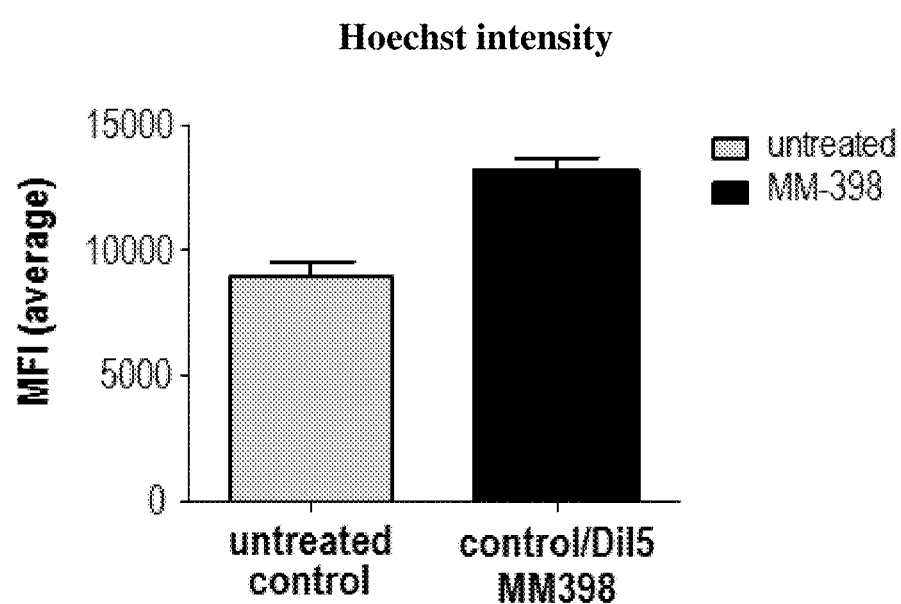
FIG. 4 shows the effect of MM-398 on perfusion of small molecule Hoechst stain.

In addition to changing the chemosensitivity of tumor cells through modification of the tumor microenvironment, lowering hypoxia can indicate improved tumor vascularization, which can facilitate delivery of small molecule therapies. MM-398 treatment led to increased microvessel density 6 days after treatment as measured by CD31 (platelet endothelial cell adhesion molecule) staining in an HT29 xenograft study. To further assess the effect of MM-398 on small molecule tumor vascularization, a Hoechst 33342 perfusion experiment was conducted. Specifically, a primary pancreatic tumor was grown in NOD-SCID mice and given one dose of MM-398 (20 mg/kg). After 24 hours, Hoechst 33342 stain was administered 20 minutes prior to sacrificing the animal. As shown in FIG. 4, the increase in stain intensity in treated mice was statistically significant, $p<0.001$. These data indicate that MM-398 modifies the tumor microenvironment in a manner that should make tumors more susceptible to agents such as 5-FU/LV, through decreasing tumor hypoxia and increasing small molecule perfusion.

Example 5

MM-398 Pharmacokinetics in Humans (Phase I)

The pharmacokinetic profile of MM-398 single agent was investigated in a phase I clinical study (PEP0201) in patients at 60, 120 or 180 mg/m² dose levels and in a phase II clinical trial in gastric cancer patients (PEP0206) at 120 mg/m². Plasma levels of total irinotecan, SN-38 and encapsulated irinotecan were measured in these studies.

The peak serum concentrations of total irinotecan ($C_{max}$) ranged from 48-79 µg/ml for 120 mg/m² of MM-398, which was approximately 50 fold higher than 125 mg/m² free irinotecan. The total irinotecan half-life ($t_{1/2}$) for MM-398 ranged from 21 to 48 hours, which was approximately 2-3 fold higher than 125 mg/m² of free irinotecan. Overall, total irinotecan exposure at one week (AUC 0-T) ranged from 1200-3000 (µg*h/ml) at a dose of 120 mg/m² of MM-398, approximately 50-100 fold higher than 300 mg/m² of free irinotecan. In contrast, SN38 $C_{max}$ levels at 120 mg/m² of MM-398 ranged from 9 to 17 ng/ml, which was approximately 50% less than free irinotecan at 125 mg/m². Overall, exposure of SN38 at one week (AUC 0-T) ranged from 474 to 997 ng*/ml and was only 1-2 fold higher than achieved by free irinotecan at 300 mg/m². For both SN38 and total irinotecan, AUC increased less than proportionally with dose of MM-398. The PK parameters of encapsulated irinotecan almost matched that of total irinotecan indicates that most of irinotecan remained encapsulated in the liposomes during circulation. The MM-398 PK parameters were not significantly changed when combined with 5-FU/LV. FIGS. 5 and 6 summarize the PK findings in previous studies of MM 398.

Example 6

Phase 1 Dose Escalation Study

A regimen combining fluorouracil, leucovorin, and MM-398 was studied in a phase 1 trial of solid tumors in 16 subjects, of whom 5 were patients with pancreatic cancer. The objective tumor response rate, duration of response, and disease control rate were efficacy endpoints of the study. Among the 15 efficacy-evaluable patients, 2 (13.3%) had confirmed PR, 9 (60.0%) had SD, and 4 (26.7%) had PD. The overall disease control rate was 73.3%. Partial response was observed in one gastric cancer patient (at 80 mg/m² dose level) and one breast cancer patient (at 100 mg/m2 dose level), with the duration of response of 142 and 76 days, respectively. Among the 6 patients who received the MTD dose of 80 mg/m², there were 1 PR, 4 SD and 1 PD. The tumor response rate and disease control rate were 16.7% and 83.3%, respectively. The main DLTs were grade 3 diarrhea, leucopenia, neutropenia and febrile neutropenia. The MTD for MM-398 was 80 mg/m².

In the phase 1 dose-escalation study of MM-398 in combination with 5-FU/LV in advanced solid tumors (PEP0203), a total of 401 episodes of AE were reported from the 16 treated subjects (safety population), of which 74 (18.4%) were of CTC grade 3 or above. Among all AEs, 231 (57.6%) were considered by the investigators to be treatment-related. The most common treatment-related AEs, included nausea (81.3%), diarrhea (75.0%), vomiting (68.8%), fatigue (43.8%), mucositis (43.8%), leucopenia (37.5%), neutropenia (37.5%), weight loss (37.5%), anemia (31.3%), and alopecia (31.3%). Acute cholinergic diarrhea was rarely observed. Table 1 provides the incidence of treatment-emergent adverse events by maximum CTC grade and by causality (incidence≥20%), as seen in the PEP0203 study. Table 2 provides the incidence of grade 3 or higher treatment-emergent adverse events seen in the 5 pancreatic cancer patients treated in the PEP0203 study.

TABLE 1

Incidence of treatment-emergent adverse events by maximum CTC grade and by causality (incidence ≥ 20%) in the PEP0203 Study

| System organ class Preferred Term | Total (N = 16) | Severity (Grade)[1] I | II | III | IV | Causality[2] Yes | No |
|---|---|---|---|---|---|---|---|
| Blood and lymphatic system disorders | | | | | | | |
| Anemia | 7 (43.8%) | 3 | 2 | 2 | 0 | 5 | 2 |
| Leucopenia | 6 (37.5%) | 0 | 3 | 2 | 1 | 6 | 0 |
| Neutropenia | 6 (37.5%) | 0 | 2 | 3 | 1 | 6 | 0 |
| Gastrointestinal disorders | | | | | | | |
| Abdominal pain | 7 (43.8%) | 3 | 2 | 2 | 0 | 3 | 4 |
| Constipation | 6 (37.5%) | 3 | 3 | 0 | 0 | 0 | 6 |
| Diarrhea | 12 (75.0%) | 3 | 4 | 5 | 0 | 12 | 0 |
| Nausea | 13 (81.3%) | 6 | 6 | 1 | 0 | 13 | 0 |
| Vomiting | 12 (75.0%) | 3 | 8 | 1 | 0 | 11 | 1 |
| General disorders and administration site conditions | | | | | | | |
| Fatigue | 8 (50.0%) | 4 | 3 | 1 | 0 | 7 | 1 |
| Mucosal inflammation | 7 (43.8%) | 4 | 3 | 0 | 0 | 7 | 0 |
| Pyrexia | 7 (43.8%) | 3 | 4 | 0 | 0 | 2 | 5 |
| Infections and infestations | | | | | | | |
| Infection | 6 (37.5%) | 0 | 3 | 3 | 0 | 2 | 4 |
| Investigations | | | | | | | |
| ALT increased | 5 (31.3%) | 3 | 2 | 0 | 0 | 4 | 1 |
| AST increased | 4 (25.0%) | 3 | 1 | 0 | 0 | 1 | 3 |
| Weight decreased | 8 (50.0%) | 4 | 4 | 0 | 0 | 6 | 2 |
| Metabolism and nutrition disorders | | | | | | | |
| Anorexia | 4 (25.0%) | 1 | 2 | 1 | 0 | 3 | 1 |
| Hypoalbuminaemia | 4 (25.0%) | 0 | 3 | 1 | 0 | 0 | 4 |
| Hypocalcaemia | 5 (31.3%) | 1 | 4 | 0 | 0 | 0 | 5 |
| Hypokalaemia | 8 (50.0%) | 2 | 0 | 5 | 1 | 2 | 6 |
| Hyponatraemia | 4 (25.0%) | 2 | 0 | 0 | 2 | 0 | 4 |
| Nervous system disorders | | | | | | | |
| Dizziness | 4 (25.0%) | 4 | 0 | 0 | 0 | 1 | 3 |
| Psychiatric disorders | | | | | | | |
| Insomnia | 4 (25.0%) | 4 | 0 | 0 | 0 | 1 | 3 |
| Respiratory, thoracic and mediastinal disorders | | | | | | | |
| Cough | 5 (31.3%) | 3 | 1 | 1 | 0 | 0 | 5 |
| Skin and subcutaneous tissue disorders | | | | | | | |
| Alopecia | 5 (31.3%) | 5 | 0 | 0 | 0 | 5 | 0 |

[1] Severity grading used the highest grading ever rated for each subject if the subject had such adverse event reported
[2] Defined as subject ever experienced AE related to the study drug in causality or not

TABLE 2

Incidence of Grade 3 or higher treatment-emergent adverse events in pancreatic cancer patients in the PEP0203 Study

| Primary system organ class Preferred term | Overall N = 5 n (%) | 60 mg/m2 N = 1 n (%) | 80 mg/m2 N = 3 n (%) | 120 mg/m2 N = 1 n (%) |
|---|---|---|---|---|
| Any primary system organ class | | | | |
| Total | 3 (60.0) | 0 | 2 (66.7) | 1 (100.0) |
| Infections and infestations | | | | |
| Total | 3 (60.0) | 0 | 2 (66.7) | 1 (100.0) |
| Hepatitis viral | 1 (20.0) | 0 | 1 (33.3) | 0 |
| Infection | 1 (20.0) | 0 | 0 | 1 (100.0) |
| Pneumonia | 1 (20.0) | 0 | 1 (33.3) | 0 |
| Septic shock | 1 (20.0) | 0 | 1 (33.3) | 0 |
| Blood and lymphatic system disorders | | | | |
| Total | 2 (40.0) | 0 | 1 (33.3) | 1 (100.0) |
| Lymphopenia | 1 (20.0) | 0 | 0 | 1 (100.0) |
| Neutropenia | 1 (20.0) | 0 | 1 (33.3) | 0 |
| White blood cell disorder | 1 (20.0) | 0 | 0 | 1 (100.0) |
| Gastrointestinal disorders | | | | |
| Total | 2 (40.0) | 0 | 1 (33.3) | 1 (100.0) |
| Diarrhea | 2 (40.0) | 0 | 1 (33.3) | 1 (100.0) |
| Abdominal pain | 1 (20.0) | 0 | 0 | 1 (100.0) |
| Gastrointestinal hemorrhage | 1 (20.0) | 0 | 1 (33.3) | 0 |

TABLE 2-continued

Incidence of Grade 3 or higher treatment-emergent adverse events in pancreatic cancer patients in the PEP0203 Study

| Primary system organ class<br>Preferred term | Overall<br>N = 5<br>n (%) | 60<br>mg/m2<br>N = 1<br>n (%) | 80<br>mg/m2<br>N = 3<br>n (%) | 120<br>mg/m2<br>N = 1<br>n (%) |
|---|---|---|---|---|
| Investigations | | | | |
| Total | 2 (40.0) | 0 | 1 (33.3) | 1 (100.0) |
| Blood bilirubin increased | 1 (20.0) | 0 | 1 (33.3) | 0 |
| Lipase increased | 1 (20.0) | 0 | 0 | 1 (100.0) |
| Neutrophil count decreased | 1 (20.0) | 0 | 0 | 1 (100.0) |
| White blood cell count decreased | 1 (20.0) | 0 | 0 | 1 (100.0) |
| Metabolism and nutrition disorders | | | | |
| Total | 2 (40.0) | 0 | 1 (33.3) | 1 (100.0) |
| Hypoalbuminaemia | 1 (20.0) | 0 | 1 (33.3) | 0 |
| Hypokalaemia | 1 (20.0) | 0 | 1 (33.3) | 0 |
| Hyponatraemia | 1 (20.0) | 0 | 0 | 1 (100.0) |
| Hypophosphataemia | 1 (20.0) | 0 | 0 | 1 (100.0) |
| Respiratory, thoracic and mediastinal disorders | | | | |
| Total | 2 (40.0) | 0 | 1 (33.3) | 1 (100.0) |
| Dyspnoea | 1 (20.0) | 0 | 0 | 1 (100.0) |
| Pleural effusion | 1 (20.0) | 0 | 1 (33.3) | 0 |
| General disorders and administration site conditions | | | | |
| Total | 1 (20.0) | 0 | 0 | 1 (100.0) |
| Death | 1 (20.0) | 0 | 0 | 1 (100.0) |

Example 7

Phase 3 Trial

The promising efficacy and safety data from the Phase 1 Trial (described above) warrant the MM-398 and 5-FU plus leucovorin combination to be explored further in a phase 3 study.

Objectives

The primary objective of the Phase 3 trial is to compare overall survival following treatment with MM-398, with or without 5-fluorouracil plus leucovorin, versus 5-fluorouracil and leucovorin in patients with metastatic pancreatic cancer that have progressed on gemcitabine based therapy. The secondary objectives include the following:

To compare time-to-event efficacy endpoints between the experimental and control arms (i.e., Progression-free survival (PFS) and Time to treatment failure (TTF));

To compare the Objective Response Rate (ORR) between the treatment arms;

To compare the tumor marker response of CA 19-9 between the treatment arms;

To compare the Clinical Benefit Response (CBR) rate between the treatment arms;

To assess patient-reported outcomes (PROs) between the treatment arms using the European Organization for Research and Treatment of Cancer (EORTC) quality-of-life core questionnaire (EORTC-QLQ-C30);

To compare the safety and adverse event profile between the treatment arms; and

To determine the pharmacokinetic properties of MM-398, as a single agent and in combination with 5-FU and leucovorin.

A key exploratory objective of this study is to explore biomarkers associated with toxicity and efficacy following treatment with MM-398 and MM-398 plus 5-FU and leucovorin.

A. Study Design

This is an open label, randomized, three arm, Phase 3 trial of MM-398, with or without 5-FU and leucovorin, versus 5-fluorouracil (5-FU) and leucovorin (also known as folinic acid), in metastatic pancreatic cancer patients who have progressed on prior gemcitabine based therapy.

Approximately 405 eligible patients will be enrolled in this global study, under the protocol version 2 or later. All patients will participate in up to 28 days of screening, during which they will be assessed for eligibility and screened for the UGT1A1*28 allele. Eligible patients will be randomized, in a 1:1:1 ratio, to one of the following treatment arms:

| | |
|---|---|
| Arm A (experimental arm): MM-398 | MM 398 120 mg/m2 IV over 90 minutes, every 3 weeks. Patients who are homozygous for UGT1A1*28 allele will receive the first cycle of therapy at a reduced dose of 80 mg/m$^2$. If the patient does not experience any drug related toxicity after the first administration of MM-398, from cycle 2 onwards, the dose may be increased in increments of 20 mg/m$^2$ up to a maximum of 120 mg/m$^2$. |
| Arm B (control arm): 5-FU and leucovorin | 5-FU 2000 mg/m$^2$ IV over 24-hours (+/−30 minutes), administered weekly for 4 weeks (days 1, 8, 15 and 22), followed by 2 weeks of rest, in a 6 weekly cycle. Levoleucovorin dosed at 200 mg/m$^2$ or the leucovorin l + d racemic mixture dosed at 400 mg/m$^2$, given IV over 30 minutes, administered weekly for 4 weeks (days 1, 8, 15 and 22), followed by 2 weeks of rest, in a 6 weekly cycle. |
| Arm C (experimental arm): MM-398, 5-FU and leucovorin | MM-398 80 mg/m$^2$ IV over 90 minutes, every 2 weeks. Patients who are homozygous for UGT1A1*28 allele and are randomized to Arm C, will receive the first cycle of therapy at a reduced dose of 60 mg/m$^2$. If the patient does not experience any drug related toxicity after the first administration of MM-398, from cycle 2 onwards, the dose may be increased to 80 mg/m$^2$.<br>5-FU 2400 mg/m$^2$ IV over 46-hours, every 2 weeks. Levoleucovorin dosed at 200 mg/m$^2$ or the l + d racemic mixture dosed at 400 mg/m$^2$, IV over 30 minutes, every 2 weeks.<br>MM-398 should be administered prior to 5-FU and leucovorin; leucovorin should always be administered prior to 5-FU. If the dosing of either MM-398 or 5-FU/leucovorin needs to be withheld, then the other drug in the combination should not be administered either. |

Patients will be evenly randomized to the treatment arms using an Interactive Web Response System (IWRS) at a central location. The randomization will be stratified based on the following prognostic factors:

Baseline albumin levels (≥4.0 g/dL vs<4.0 g/dL)
KPS (70 and 80 vs≥90)
Ethnicity (Caucasian vs East Asian vs All Others)

Therapy will be administered in cycles. Patients will be treated until disease progression (radiologic or clinical deterioration), intolerable toxicity or other reasons for study termination. Tumor responses will be assessed, using the RECIST guidelines (Eisenhauer, E. A., et al., "New response evaluation criteria in solid tumors: Revised RECIST guideline (version 1.1). *European Journal of Cancer*, 2009. 45: pp. 228-247) every 6 weeks or sooner if disease progression based on clinical signs and symptoms is evident. Tumor measurement images will be collected and stored on all patients throughout the study. However, all treatment decisions will be based on the local radiologist and/or PI assessment of disease status. An independent review of the scans may be performed in the event that an independent analysis of ORR and/or PFS is necessary.

Following treatment discontinuation a 30-day post therapy follow up visit is required. Subsequently, all patients will be followed-up every 1 month for overall survival (by phone or visit to the study site) until death or study closure, whichever occurs first. Patients, who withdraw from study treatment due to reasons other than objective disease progression, should continue to be assessed every 6 weeks during the follow-up period for radiologic progression (including patients who discontinue due to symptomatic deterioration).

All patients will be asked to complete a pain assessment and analgesic consumption diary throughout their participation in the study, which will document the patient's assessment of their pain intensity and daily analgesic consumption. Patient responses will be used for assessment of the clinical benefit response along with the other parameters. All patients will also be required to complete the EORTC-QLQ-C30 questionnaire for assessing quality of life.

In order to address the exploratory objectives of this study, all sites will be required to participate in the companion translational research (TR) protocol (MM-398-07-03-01.TR), unless prohibited by local regulations. Participation is this study will be optional for patients and they will be required to provide a separate consent for the translational research.

Figure 7:
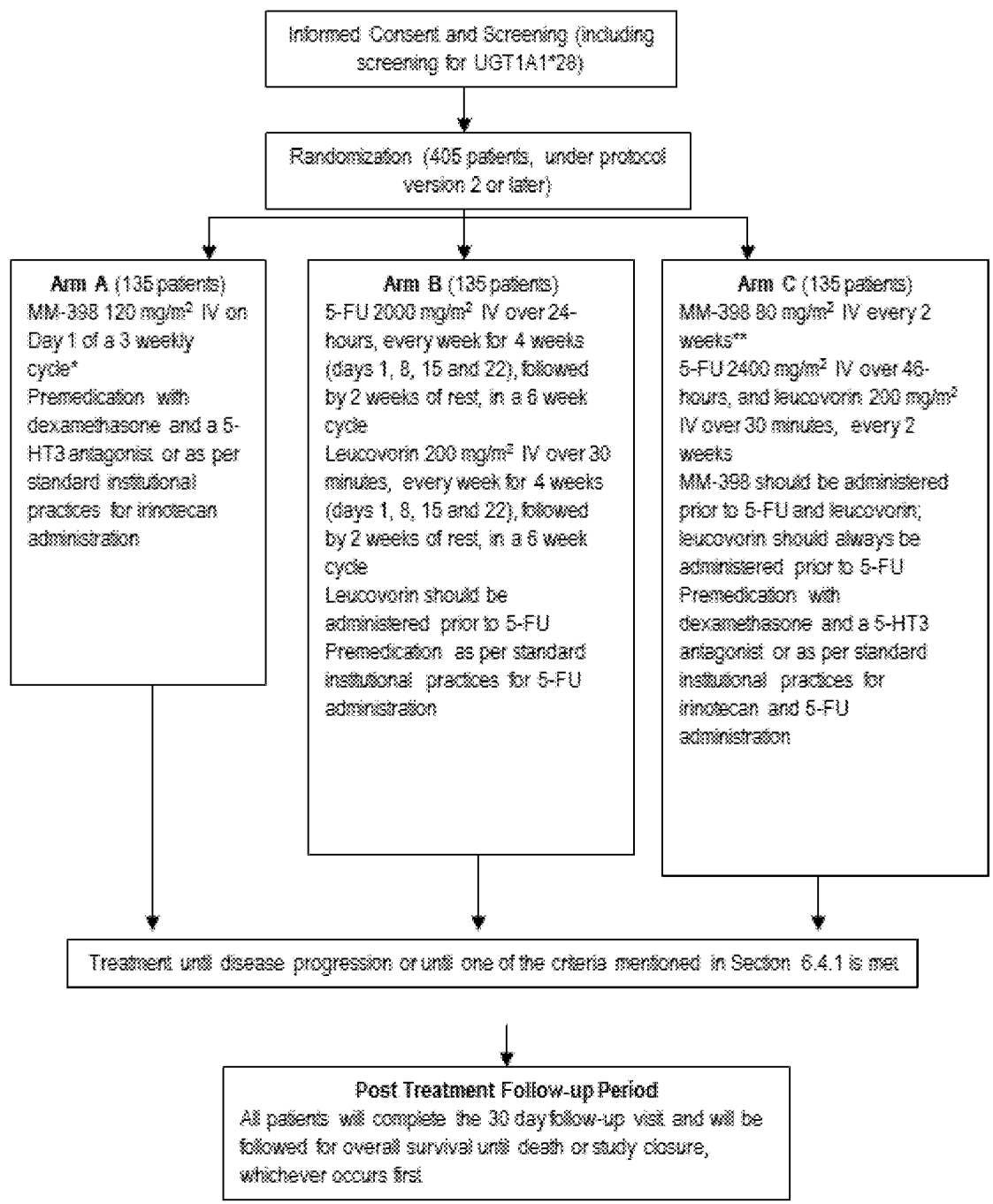
FIG. 7 is a schematic illustration of a Phase 3 study design.

The primary analysis of OS will take place once at least 305 deaths events have occurred in patients enrolled under protocol version 2 or later. Patients receiving study treatment at the time of primary analysis for OS will continue to receive treatment until one of the criteria for discontinuation is met. During the course of the study, regular review of safety data will be conducted by an independent data safety monitoring board (DSMB). FIG. 7 illustrates the study design. Patients who are homozygous for UGT1A1*28 allele and are randomized to Arm A, will receive the first cycle of therapy at a reduced dose of 80 mg/m2 (indicated by *). If the patient does not experience any drug related toxicity after the first administration of MM-398, from cycle 2 onwards, the dose may be increased in increments of 20 mg/m$^2$, up to a maximum of 120 mg/m$^2$. Patients who are homozygous for UGT1A1*28 allele and are randomized to Arm C, will receive the first cycle of therapy at a reduced dose of 60 mg/m$^2$ (indicated by **). If the patient does not experience any drug related toxicity after the first administration of MM-398, from cycle 2 onwards, the dose may be increased to 80 mg/m$^2$.

B. Patient Selection and Discontinuation

Approximately 405 patients will be enrolled globally in this study, under the protocol version 2 or later. In order to be included in the study, patients must have/be:

1. Histologically or cytologically confirmed adenocarcinoma of exocrine pancreas
2. Documented metastatic disease; disease status may be measurable or non-measurable as defined by RECIST v1.1 guidelines
3. Documented disease progression after prior gemcitabine or gemcitabine containing therapy, in locally advanced or metastatic setting. Examples of permitted therapies include, but are not limited to:
   Single agent gemcitabine
   Any one gemcitabine-based regimen, with or without maintenance gemcitabine
   Single agent gemcitabine to which a platinum agent, a fluoropyrimidine, or erlotinib was subsequently added
   Gemcitabine administered in the adjuvant setting if disease recurrence occurred within 6 months of completing the adjuvant therapy
4. Karnofsky Performance Status (KPS)≥70
5. Adequate bone marrow reserves as evidenced by:
   ANC>1,500 cells/µl without the use of hematopoietic growth factors; and
   Platelet count>100,000 cells/µl; and
   Hemoglobin>9 g/dL (blood transfusions are permitted for patients with hemoglobin levels below 9 g/dL)
6. Adequate hepatic function as evidenced by:
   Serum total bilirubin within normal range for the institution (biliary drainage is allowed for biliary obstruction)
   Albumin levels≥3.0 g/dL
   Aspartate aminotransferase (AST) and alanine aminotransferase (ALT)≤2.5×ULN (≤5×ULN is acceptable if liver metastases are present)
7. Adequate renal function as evidenced by a serum creatinine≤1.5×ULN
8. Normal ECG or ECG without any clinically significant findings
9. Recovered from the effects of any prior surgery, radiotherapy or other anti-neoplastic therapy
10. At least 18 years of age
11. Able to understand and sign an informed consent (or have a legal representative who is able to do so)

Patients must meet all the inclusion criteria listed above and none of the following exclusion criteria:

1. Active CNS metastases (indicated by clinical symptoms, cerebral edema, steroid requirement, or progressive disease)
2. Clinically significant gastrointestinal disorder including hepatic disorders, bleeding, inflammation, occlusion, or diarrhea>grade 1
3. History of any second malignancy in the last 5 years; subjects with prior history of in-situ cancer or basal or squamous cell skin cancer are eligible. Subjects with other malignancies are eligible if they have been continuously disease free for at least 5 years.
4. Severe arterial thromboembolic events (myocardial infarction, unstable angina pectoris, stroke) less than 6 months before inclusion
5. NYHA Class III or IV congestive heart failure, ventricular arrhythmias or uncontrolled blood pressure
6. Active infection or an unexplained fever>38.5° C. during screening visits or on the first scheduled day of dosing (at the discretion of the investigator, patients with tumor fever may be enrolled), which in the investigator's opinion might compromise the patient's participation in the trial or affect the study outcome
7. Known hypersensitivity to any of the components of MM-398, other liposomal products, fluropyrimidines or leucovorin
8. Investigational therapy administered within 4 weeks, or within a time interval less than at least 5 half-lives of the investigational agent, whichever is longer, prior to the first scheduled day of dosing in this study
9. Any other medical or social condition deemed by the Investigator to be likely to interfere with a patient's ability to sign informed consent, cooperate and participate in the study, or interfere with the interpretation of the results
10. Pregnant or breast feeding; females of child-bearing potential must test negative for pregnancy at the time of enrollment based on a urine or serum pregnancy test. Both male and female patients of reproductive potential must agree to use a reliable method of birth control, during the study and for 3 months following the last dose of study drug.

The criteria for enrollment must be followed explicitly. Patients will be discontinued from the study treatment in the following circumstances:

Patient has evidence of disease progression based on RECIST v1.1 criteria

Patient shows symptomatic deterioration

Patient experiences intolerable toxicity, or an adverse event which requires:
  A third dose reduction
  Treatment to be withheld for more than 21 days from the start of next cycle, unless, in the opinion of the investigator, the patient is receiving benefit from study treatment Patient is significantly non-compliant with study procedures per PI assessment The patient or patient's attending physician requests that the patient be withdrawn from the study treatment The investigator or Sponsor, for any reason, but considering the rights, safety and well-being of the patient(s) and in accordance with ICH/GCP Guidelines and local regulations, stops the study or stops the patient's participation in the study If a patient is lost to follow-up or withdraws from study treatment, attempts should be made to contact the patient to determine the reason for discontinuation. For patients who are lost to follow-up, at least 3 documented attempts, including one via certified mail, should be made to contact the patient before considering the patient lost to follow-up. If a patient discontinues study treatment due to reasons other than objective disease progression, the patient should continue to have radiological disease assessment every 6 weeks until objective disease progression is observed.

All patients who discontinue study treatment should continue to be followed-up as required by the protocol. The only circumstance under which a patient should not be followed for study endpoints is when the patient has withdrawn consent. Withdrawal of consent should be a patient initiated decision and should mean, not only that the patient wishes to discontinue study treatment and follow-up visits but also that the investigator is no longer authorized to make further efforts to contact the patient, including any efforts to identify their survival status.

C. Method of Assigning Patients to Treatment Groups

After all screening assessments have been completed and UGT1A1*28 results are available, patients will be randomized using a computerized interactive web response system (IWRS), in a 1:1:1 ratio, to one of the following treatment arms:

Arm A (experimental arm): MM-398
  Arm B (control arm): 5-FU and leucovorin
  Arm C (experimental arm): MM-398, 5-FU and leucovorin Randomization must occur within 7 days of planned dosing. The randomization will be stratified based on the following prognostic factors:

Baseline albumin levels (≥4.0 g/dL vs<4.0 g/dL)
  KPS (70 and 80 vs≥90)
  Ethnicity (Caucasian vs East Asian vs All Others)

Description of MM-398

MM-398 is irinotecan (also known as CPT-11) encapsulated in a liposomal drug delivery system. It will be supplied as sterile, single-use vials containing 9.5 mL of MM-398 at a concentration of 5 mg/mL. The vials contain a 0.5 mL excess to facilitate the withdrawal of the label amount from each 10 mL vial.

MM-398 must be stored refrigerated at 2 to 8° C., with protection from light. Light protection is not required during infusion. MM-398 must not be frozen. Responsible individuals should inspect vial contents for particulate matter before and after they withdraw the drug product from a vial into a syringe.

MM-398 must be diluted prior to administration. The diluted solution is physically and chemically stable for 6 hours at room temperature (15-30° C.), but it is preferred to be stored at refrigerated temperatures (2-8° C.), and protected from light. The diluted solution must not be frozen. Because of possible microbial contamination during dilution, it is advisable to use the diluted solution within 24 hours if refrigerated (2-8° C.), and within 6 hours if kept at room temperature (15-30° C.).

Twenty vials of MM-398 will be packaged in a cardboard container. The individual vials, as well as the outside of the cardboard container, will be labeled in accordance with local regulatory requirements.

MM-398 will be dosed and administered as follows. All patients will be screened for UGT1A1*28 allele at baseline.

| | |
|---|---|
| Arm A | Patients who do not have the homozygous allele for UGT1A1*28 will receive MM-398 at a dose of 120 mg/m². Any patient who is homozygous for UGT1A1*28 will receive the first cycle of therapy at a reduced dose of 80 mg/m². If the patient does not experience any drug related toxicity after the first administration of MM-398, from cycle 2 onwards, their dose can be increased in increments of 20 mg/m², up to a maximum of 120 mg/m². |
| Arm C | Patients who do not have the homozygous allele for UGT1A1*28 will receive MM-398 at a dose of 80 mg/m². Patients who are homozygous for UGT1A1*28 allele and are randomized to Arm C, will receive the first cycle of therapy at a reduced dose of 60 mg/m². If the patient does not experience any drug related toxicity after the first administration of MM-398, from cycle 2 onwards, the dose may be increased to 80 mg/m². MM-398 should be administered prior to 5-FU and leucovorin administration. |

In Arm A, MM-398 will be administered by IV infusion over 90 minutes on the first day of each 3 week cycle, at the investigational site. In Arm C, MM-398 will be administered by an IV infusion over 90 minutes for the first cycle; the infusion time could be reduced to 60 minutes from cycle 2 onwards, if no acute infusion reaction has occurred in cycle 1. Cycle duration is 3 weeks for Arm A and 2 weeks for Arm C. The first cycle Day 1 is a fixed day; subsequent doses should be administered on the first day of each cycle+/−3 days.

Prior to administration, the appropriate dose of MM-398 must be diluted in 5% Dextrose Injection solution (D5W) to a final volume of 500 mL. Care should be taken not to use in-line filters or any diluents other than D5W. MM-398 can be administered using standard PVC-containing intravenous administration bags and tubing.

The actual dose of MM-398 to be administered will be determined by calculating the patient's body surface area at the beginning of each cycle. A +/−5% variance in the calculated total dose will be allowed for ease of dose administration. Since MM-398 vials are single-use vials, site staff must not store any unused portion of a vial for future use and they must discard unused portions of the product.

All patients must be premedicated prior to MM-398 infusion with standard doses of dexamethasone and a 5-HT3 antagonist or other anti-emetics as per standard institutional practices for irinotecan administration. Atropine may be prescribed prophylactically for patients who experienced acute cholinergic symptoms in the previous cycles.

D. Description of 5-FU and Leucovorin

5-Fluorouracil is a pyrimidine antagonist that interferes with nucleic acid biosynthesis. The deoxyribonucleotide of the drug inhibits thymidylate synthetase, thus inhibiting the formation of thymidylic acid from deoxyuridylic acid, thus interfering in the synthesis of DNA. It also interferes with RNA synthesis.

Leucovorin acts as a biochemical cofactor for 1-carbon transfer reactions in the synthesis of purines and pyrimidines. Leucovorin does not require the enzyme dihydrofolate reductase (DHFR) for conversion to tetrahydrofolic acid. The effects of methotrexate and other DHFR-antagonists are inhibited by leucovorin. Leucovorin can potentiate the cytotoxic effects of fluorinated pyrimidines (i.e., fluorouracil and floxuridine). After 5-FU is activated within the cell, it is accompanied by a folate cofactor, and inhibits the enzyme thymidylate synthetase, thus inhibiting pyrimidine synthesis. Leucovorin increases the folate pool, thereby increasing the binding of folate cofactor and active 5-FU with thymidylate synthetase.

FU and leucovorin will be stored and handled according to the country specific package inserts. Commercially available 5-FU and leucovorin will be provided to all patients in the study who are randomized to Arm B and Arm C.

5-FU and leucovorin will be dosed and administered as follows.

| | |
|---|---|
| Arm B | 5-FU will be administered at a dose of 2000 mg/m$^2$ as an IV infusion over 24-hours, (+/−30 minutes), every week for 4 weeks (days 1, 8, 15 and 22), followed by 2 weeks of rest, in a 6 week cycle<br>Leucovorin will be administered at a dose of 200 mg/m$^2$ (l form) or 400 mg/m$^2$ (l + d racemic form) as an IV infusion over 30 minutes, every week for 4 weeks (days 1, 8, 15 and 22), followed by 2 weeks of rest, in a 6 week cycle |
| Arm C | 5-FU will be administered at a dose of 2400 mg/m$^2$ as an IV infusion over 46-hours, (+/−60 minutes), every 2 weeks<br>Leucovorin will be administered at a dose of 200 mg/m$^2$ (l form) or 400 mg/m$^2$ (l + d racemic form) as an IV infusion over 30 minutes, every 2 weeks |

Leucovorin should be reconstituted per the instructions on the package inset or standard institutional guidelines for reconstitution of leucovorin. Leucovorin should be administered prior to the 5-FU infusion.

Actual dose of 5-FU and leucovorin to be administered will be determined by calculating the patient's body surface area prior to each cycle. A +/−5% variance in the calculated total dose will be allowed for ease of dose administration.

After cycle 1, for the start of each new cycle, a window period of +/−3 days will be permitted, and a window period of +/−1 day will be permitted for the Day 8, 15 and 22 infusions.

All patients must be premedicated prior to 5-FU and leucovorin infusion with standard doses of dexamethasone, prochlorperazine or equivalent other anti-emetics as per standard institutional practices for 5-FU administration.

E. Important Treatment Considerations with MM-398

Data from previous MM-398 studies does not show any unexpected toxicity when compared to the active ingredient, irinotecan, which has been studied extensively. The warnings and precautions for the use of irinotecan and the treatment procedures for managing those toxicities are provided below.

Diarrhea

Irinotecan can induce both early and late forms of diarrhea that appear to be mediated by different mechanisms. Early diarrhea (occurring during or shortly after infusion of irinotecan) is cholinergic in nature. It is usually transient and only infrequently severe. It may be accompanied by symptoms of rhinitis, increased salivation, miosis, lacrimation, diaphoresis, flushing, and intestinal hyper-peristalsis that can cause abdominal cramping. For patients who experienced early cholinergic symptoms during the previous cycle of MM-398, prophylactic administration of atropine will be given at the discretion of the investigator.

Late diarrhea (generally occurring more than 24 hours after administration of irinotecan) can be life threatening since it may be prolonged and may lead to dehydration, electrolyte imbalance, or sepsis. Late diarrhea should be treated promptly with loperamide, and octreotide should be considered if diarrhea persists after loperamide. Loss of fluids and electrolytes associated with persistent or severe diarrhea can result in life threatening dehydration, renal insufficiency, and electrolyte imbalances, and may contribute to cardiovascular morbidity. The risk of infectious complications is increased, which can lead to sepsis in patients with chemotherapy-induced neutropenia. Patients with diarrhea should be carefully monitored, given fluid and electrolyte replacement if they become dehydrated, and given antibiotic support if they develop ileus, fever, or severe neutropenia.

Neutropenia

Deaths due to sepsis following severe neutropenia have been reported in patients treated with irinotecan. Neutropenic complications should be managed promptly with antibiotic support. G-CSF may be used to manage neutropenia, with discretion. Patients, who are known to have experienced Grade 3 or 4 neutropenia while receiving prior anti-neoplastic therapy, should be monitored carefully and managed.

Hypersensitivity

Hypersensitivity reactions including severe anaphylactic or anaphylactoid reactions have been observed. Suspected drugs should be withheld immediately and aggressive therapy should be given if hypersensitivity reactions occur.

Colitis/Ileus

Cases of colitis complicated by ulceration, bleeding, ileus, and infection have been observed. Patients experiencing ileus should receive prompt antibiotic support.

Thromboembolism

Thromboembolic events have been observed in patients receiving irinotecan-containing regimens; the specific cause of these events has not been determined.

Pregnancy

The pregnancy category of irinotecan is D. Women of childbearing potential should be advised to avoid becoming pregnant while receiving treatment with irinotecan. If a pregnancy is reported, treatment should be discontinued. The patient should be withdrawn from the study, and the pregnancy should be followed until the outcome becomes known.

Care of Intravenous Site

Care should be taken to avoid extravasation, and the infusion site should be monitored for signs of inflammation. Should extravasation occur, flushing the site with sterile saline and applications of ice are recommended.

Patients at Particular Risk

In clinical trials of the weekly schedule of irinotecan, it has been noted that patients with modestly elevated baseline serum total bilirubin levels (1.0 to 2.0 mg/dL) have had a significantly greater likelihood of experiencing first-cycle grade 3 or 4 neutropenia than those with bilirubin levels that were less than 1.0 mg/dL (50.0% [19/38] versus 17.7% [47/226]; p<0.001). Patients with abnormal glucuronidation of bilirubin, such as those with Gilbert's syndrome, may also be at greater risk of myelosuppression when receiving therapy with irinotecan.

Acute Infusion Associated Reactions

Acute infusion-associated reactions characterized by flushing, shortness of breath, facial swelling, headache, chills, back pain, tightness of chest or throat, and hypotension have been reported in a small number of patients treated with liposome drugs. In most patients, these reactions generally resolve within 24 hours after the infusion is terminated. In some patients, the reaction resolves by slowing the rate of infusion. Most patients who experienced acute infusion reactions to liposome drugs are able to tolerate further infusions without complications.

Other Toxicity Potential

MM-398, the new liposome formulation of irinotecan, is different from irinotecan in unencapsulated formulation, so there is a potential for toxicities other than those caused by irinotecan. All patients should be monitored closely for signs and symptoms indicative of drug toxicity, particularly during the initial administration of treatment.

F. Dose Modification Requirements

Dosing may be held for up to 3 weeks from when it was due, to allow for recovery from toxicity related to the study treatments. If the time required for recovery from toxicity is more than 3 weeks, the patient should be discontinued from the study, unless the patient is benefiting from the study treatment, in which case the patient's continuation on study should be discussed between Investigator and Sponsor or its designee regarding risks and benefits of continuation. If a patient's dose is reduced during the study due to toxicity, it should remain reduced for the duration of the study; dose re-escalation to an earlier dose is not permitted. Any patient who has 2 dose reductions and experiences an adverse event that would require a third dose reduction must be discontinued from study treatment.

Infusion reactions will be monitored. Infusion reactions will be defined according to the National Cancer Institute CTCAE (Version 4.0) definition of an allergic reaction/infusion reaction and anaphylaxis, as defined below:

---

Grade 1: Transient flushing or rash, drug fever <38° C. (<100.4° F.); intervention not indicated
Grade 2: Intervention or infusion interruption indicated; responds promptly to symptomatic treatment (e.g., antihistamines, NSAIDS, narcotics); prophylactic medications indicated for <24 hrs
Grade 3: Symptomatic bronchospasm, with or without urticaria; parenteral intervention indicated; allergy-related edema/angioedema; hypotension
Grade 4: Life-threatening consequences; urgent intervention indicated

---

Study site policies or the following treatment guidelines shall be used for the management of infusion reactions.

---

| | |
|---|---|
| Grade 1 | Slow infusion rate by 50% |
| | Monitor patient every 15 minutes for worsening of condition |
| Grade 2 | Stop infusion |
| | Administer diphenhydramine hydrochloride 50 mg IV, acetaminophen 650 mg orally, and oxygen |
| | Resume infusion at 50% of the prior rate once infusion reaction has resolved |
| | Monitor patient every 15 minutes for worsening of condition |
| | For all subsequent infusions, premedicate with diphenhydramine hydrochloride 25-50 mg IV |
| Grade 3 | Stop infusion and disconnect infusion tubing from patient |
| | Administer diphenhydramine hydrochloride 50 mg IV, dexamethasone 10 mg IV, bronchodilators for bronchospasm, and other medications or oxygen as medically necessary |
| | No further treatment with MM-398 will be permitted |
| Grade 4 | Stop the infusion and disconnect infusion tubing from patient |
| | Administer epinephrine, bronchodilators or oxygen as indicated for bronchospasm |
| | Administer diphenhydramine hydrochloride 50 mg IV, dexamethasone 10 mg IV |
| | Consider hospital admission for observation |
| | No further treatment with MM-398 will be permitted |

For patients who experience a Grade 1 or Grade 2 infusion reaction, future infusions may be administered at a reduced rate (over 120 minutes), with discretion.

For patients who experience a second grade 1 or 2 infusion reaction, administer dexamethasone 10 mg IV. All subsequent infusions should be premedicated with diphenhydramine hydrochloride 50 mg IV, dexamethasone 10 mg IV, and acetaminophen 650 mg orally.

G. MM-398 Dose Modifications for Hematological Toxicities

Prior to initiating a new cycle of therapy, the patients must have:

ANC≥1500/mm$^3$

Platelet count≥100,000/mm$^3$

Treatment should be delayed to allow sufficient time for recovery and upon recovery, treatment should be administered according to the guidelines in the tables below. If the patient had febrile neutropenia, the ANC must have resolved to ≥1500/mm$^3$ and the patient must have recovered from infection.

TABLE

MM-398 Dose Modifications for Neutrophil Count

| | MM-398 Dose for Next Cycle[a] | | |
|---|---|---|---|
| ANC: cells/mm$^3$ (Worst CTCAE grade) | Arm A: Patients Not Homozygous for UGT1A1*28 | Arm A: Patients Homozygous for UGT1A1*28 [d] Arm C: Patients Not Homozygous for UGT1A1*28 | Arm C: Patients Homozygous for UGT1A1*28 [d] |
| ≥1000 to 1999 (Grade 1 or 2) | 100% of previous dose | 100% of previous dose | 100% of previous dose |
| <1000 (Grade 3/4) or febrile neutropenia | Reduce dose by 20 mg/m$^2$ to a minimum dose of 80 mg/m$^2$ [b] | Reduce dose to 60 mg/m$^2$ for the first occurrence and to 50 mg/m$^2$ for the second occurrence [c, d] | Reduce dose to 50 mg/m$^2$ for the first occurrence and to 40 mg/m$^2$ for the second occurrence [e, d] |

[a] All dose modifications should be based on the worst preceding toxicity
[b] Patients who require a further dose reduction beyond 80 mg/m$^2$ must be withdrawn from the study
[c] Patients who require a further dose reduction beyond 50 mg/m$^2$ must be withdrawn from the study
[d] Patients who are homozygous for UGT1A1*28 and have had their dose increased should be dose reduced per guidelines for patients who are not homozygous for UGT1A1*28
[e] Patients who require a further dose reduction beyond 40 mg/m$^2$ must be withdrawn from the study

TABLE

MM-398 Dose Modifications for Other Hematologic Toxicity

MM-398 Dose for Next Cycle[a]

| Worst Toxicity CTCAE Grade | Arm A: Patients Not Homozygous for UGT1A1*28 | Arm C: Patients Not Homozygous for UGT1A1*28 | Arm A: Patients Homozygous for UGT1A1*28 [d] Arm C: Patients Homozygous for UGT1A1*28 [d] |
|---|---|---|---|
| ≤Grade 2 | 100% of previous dose | 100% of previous dose | 100% of previous dose |
| Grade 3/4 | Reduce dose by 20 mg/m² to a minimum dose of 80 mg/m² [b] | Reduce dose to 60 mg/m² for the first occurrence and to 50 mg/m² for the second occurrence[c, d] | Reduce dose to 50 mg/m² for the first occurrence and to 40 mg/m² for the second occurrence [e, d] |

[a]All dose modifications should be based on the worst preceding toxicity
[b]Patients who require a further dose reduction beyond 80 mg/m2 must be withdrawn from the study
[c]Patients who require a further dose reduction beyond 50 mg/m2 must be withdrawn from the study
[d]Patients who are homozygous for UGT1A1*28 and have had their dose increased should be dose reduced per guidelines for patients who are not homozygous for UGT1A1*28
[e]Patients who require a further dose reduction beyond 40 mg/m² must be withdrawn from the study

H. MM-398 Dose Modifications for Non-Hematological Toxicities

Treatment should be delayed until diarrhea resolves to ≤Grade 1, and for other Grade 3 or 4 non-hematological toxicities, until they resolve to Grade 1 or baseline. Guidelines for dose adjustment of MM-398 for drug related diarrhea and other Grade 3 or 4 non-hematological toxicities are provided below. Infusion reactions should be handled as described above.

TABLE

MM-398 Dose Modifications for Diarrhea

MM-398 Dose for Next Cycle[a]

| Worst Toxicity CTCAE Grade | Arm A: Patients Not Homozygous for UGT1A1*28 | Arm C: Patients Not Homozygous for UGT1A1*28 | Arm A: Patients Homozygous for UGT1A1*28 [d] Arm C: Patients Homozygous for UGT1A1*28 [d] |
|---|---|---|---|
| Grade 1 or 2 (2-3 stools/day > pretreatment or 4-6 stools/day > pretreatment) | 100% of previous dose | 100% of previous dose | 100% of previous dose |
| Grade 3 (7-9 stools/day > pretreatment) or Grade 4 (>10 stools/day > pretreatment) | Reduce dose by 20 mg/m² to a minimum dose of 80 mg/m² [b] | Reduce dose to 60 mg/m² for the first occurrence and to 50 mg/m² for the second occurrence[c, d] | Reduce dose to 50 mg/m² for the first occurrence and to 40 mg/m² for the second occurrence [e, d] |

[a]All dose modifications should be based on the worst preceding toxicity
[b]Patients who require a further dose reduction beyond 80 mg/m² must be withdrawn from the study
[c]Patients who require a further dose reduction beyond 50 mg/m² must be withdrawn from the study
[d]Patients who are homozygous for UGT1A1*28 and have had their dose increased should be dose reduced per guidelines for patients who are not homozygous for UGT1A1*28
[e]Patients who require a further dose reduction beyond 40 mg/m² must be withdrawn from the study

TABLE

MM-398 Dose Modifications for Non-Hematological Toxicities Other than Diarrhea, Asthenia and Grade 3 Anorexia[d]

MM-398 Dose for Next Cycle[a]

| Worst Toxicity CTCAE Grade | Arm A: Patients Not Homozygous for UGT1A1*28 | Arm C: Patients Not Homozygous for UGT1A1*28 | Arm A: Patients Homozygous for UGT1A1*28 [e] Arm C: Patients Homozygous for UGT1A1*28 [e] |
|---|---|---|---|
| Grade 1 or 2 | 100% of previous dose | 100% of previous dose | 100% of previous dose |
| Grade 3 or 4 (except nausea and vomiting) | Reduce dose by 20 mg/m² to a minimum dose of 80 mg/m² [b] | Reduce dose to 60 mg/m² for the first occurrence and to 50 mg/m² for the second occurrence [c, e] | Reduce dose to 50 mg/m² for the first occurrence and to 40 mg/m² for the second occurrence [f, e] |
| Grade 3 or 4 nausea and or vomiting despite anti emetic therapy | Optimize anti-emetic therapy AND reduce dose by 20 mg/m to a minimum dose of 80 mg/m² [b] | Optimize anti-emetic therapy AND reduce dose to 60 mg/m²; if the patient is already receiving 60 mg/m², reduce dose to 50 mg/m² [c, e] | Optimize anti-emetic therapy AND reduce dose to 50 mg/m²; if the patient is already receiving 50 mg/m², reduce dose to 40 mg/m² [f, e] |

[a]All dose modifications should be based on the worst preceding toxicity
[b]Patients who require a further dose reduction beyond 80 mg/m² must be withdrawn from the study
[c]Patients who require a further dose reduction beyond 50 mg/m² must be withdrawn from the study
[d]Asthenia and Grade 3 Anorexia do not require dose modification
[e]Patients who are homozygous for UGT1A1*28 and have had their dose increased should be dose reduced per guidelines for patients who are not homozygous for UGT1A1*28
[f]Patients who require a further dose reduction beyond 40 mg/m² must be withdrawn from the study

I. 5-FU and Leucovorin Dose Modifications (Arm B and Arm C)

Guidelines for 5-FU dose modifications are provided below. No dose adjustments for toxicity are required for leucovorin. Leucovorin must be given immediately prior to each 5-FU dose; hence, if 5-FU dose is held, leucovorin dose should be held as well. In case a patient experiences an infusion reaction, either institutional guidelines or the guidelines provided for MM-398 infusion reaction management should be used.

J. 5-FU Dose Modifications for Hematological Toxicities

Prior to the next dose in a cycle or prior to initiating a new cycle of therapy, the patients must have:

ANC≥1500/mm³

WBC≥3500/mm³

Platelet count≥75,000/mm³ (according to the European summary of product characteristics for 5-FU, the platelets should have recovered to ≥100,000/mm³ prior to initiating therapy)

Treatment should be delayed to allow sufficient time for recovery and upon recovery, treatment should be administered according to the guidelines provided in the table below. The duration of the cycles is fixed at 6 weeks, and if a patient is unable to receive the D8, D15 or D22 dose due to toxicity, the dose will be considered as skipped.

TABLE

5-FU Dose Modifications for Hematological Toxicities (Arm B & C)

| ANC (cells/mm³) | Platelets (cells/mm³) | 5-FU Dose for D8, D15, D22[a] | 5-FU Dose for Next Cycle[a] |
|---|---|---|---|
| ≥1000 | and ≥50,000 | 100% of previous dose | 100% of previous dose |
| 500-999 | Or <50,000-25,000 | Hold; when resolved, reduce dose by 25%[b] | Reduce dose by 25%[b] |
| <500 or febrile neutropenia | Or <25,000 or thrombocytopenia with bleeding | Hold dose; when resolved, reduce dose by 25%[b] | Reduce dose by 25%[b] |

[a]All dose modifications should be based on the worst preceding toxicity [b]Patients who require more than 2 dose reductions must be withdrawn from the study K. 5-FU Dose Modifications for Non-Hematological Toxicities Treatment should be delayed until all Grade 3 or 4 non-hematological toxicities resolve to Grade 1 or baseline. Guidelines for dose adjustment of 5-FU related toxicities are provided below. The duration of the cycles is fixed at 6 weeks, and if a patient is unable to receive the D8, D15 or D22 dose due to toxicity, the dose will be considered as skipped.

TABLE

5-FU Dose Modifications for Non-Hematological Toxicities Other than Asthenia and Grade 3 Anorexia[c] (Arm B & C)

| Worst Toxicity CTCAE Grade | 5-FU Dose for D8, D15, D22[a] | 5-FU Dose for Next Cycle[a] |
|---|---|---|
| Grade 1 or 2 | 100% of previous dose, except for Grade 2 hand foot syndrome, Grade 2 cardiac toxicity, or any grade neurocerebellar toxicity | 100% of previous dose, except for Grade 2 hand and foot syndrome, Grade 2 cardiac toxicity, or any grade neurocerebellar toxicity |
| Grade 2 hand foot syndrome | Reduce dose by 25%[b] | Reduce dose by 25%[b] |
| Any grade neurocerebellar or ≥ Grade 2 cardiac toxicity | Discontinue therapy | Discontinue therapy |
| Grade 3 or 4 | Hold; when resolved, reduce dose by 25%[b], except for Grade 3 or 4 hand foot syndrome | Reduce dose by 25%[b], except for Grade 3 or 4 hand foot syndrome |
| Grade 3 or 4 hand foot syndrome | Discontinue therapy | Discontinue therapy |

[a]All dose modifications should be based on the worst preceding toxicity
[b] Patients who require more than 2 dose reductions must be withdrawn from the study
[c]Asthenia and Grade 3 Anorexia do not require dose modification L. Other Toxicities Requiring Special Attention For both 5-FU and MM-398 treatment arms, QTc prolongation that occurs in the setting of diarrhea induced electrolyte imbalance should be treated by with appropriate electrolyte repletion. Once the underlying abnormality is corrected and the ECG abnormalities have reversed, treatment may continue under careful monitoring and with appropriate dose modification for diarrhea as described above.

M. Concomitant Therapy

All concurrent medical conditions and complications of the underlying malignancy will be treated at the discretion of the Investigator according to acceptable local standards of medical care. Patients should receive analgesics, antiemetics, antibiotics, anti-pyretics, and blood products as necessary. Although warfarin-type anticoagulant therapies are permitted, careful monitoring of coagulation parameters is imperative, in order to avoid complications of any possible drug interactions. All concomitant medications, including transfusions of blood products, will be recorded on the appropriate case report form.

Guidelines for treating certain medical conditions are discussed below; however, institutional guidelines for the treatment of these conditions may also be used. The concomitant therapies that warrant special attention are discussed below.

Antiemetic Medications

Dexamethasone and a 5-HT3 blocker (e.g., ondansetron or granisetron) will be administered to all patients as pre-medications unless contraindicated for the individual patient. Antiemetics will also be prescribed as clinically indicated during the study period.

Colony Stimulating Factors

Use of granulocyte colony-stimulating factors (G-CSF) is permitted to treat patients with neutropenia or neutropenic fever; prophylactic use of G-CSF will be permitted only in those patients who have had at least one episode of grade 3 or 4 neutropenia or neutropenic fever while receiving study therapy or have had documented grade 3 or 4 neutropenia or neutropenic fever while receiving prior anti-neoplastic therapy.

Therapy for Diarrhea

Acute diarrhea and abdominal cramps, developing during or within 24 hours after MM-398 administration, may occur as part of a cholinergic syndrome. The syndrome will be treated with atropine. Prophylactic or therapeutic administration of atropine should be considered in patients experiencing cholinergic symptoms during the study.

Diarrhea can be debilitating and on rare occasions is potentially life-threatening. Guidelines developed by an ASCO panel for treating chemotherapy-induced diarrhea are abstracted below.

TABLE

Recommendations for Management of Chemotherapy Induced Diarrhea

| Clinical Presentation | Intervention |
|---|---|
| Diarrhea, any grade | Oral loperamide (2 mg every 2 hours for irinotecan induced diarrhea; 2 mg every 4 hours for 5-FU induced diarrhea): continue until diarrhea-free for ≥12 hours |
| Diarrhea persists on loperamide for >24 hours | Oral fluoroquinolone x 7 days |
| Diarrhea persists on loperamide for >48 hours | Stop loperamide; hospitalize patient; administer IV fluids |
| ANC <500 cells/μL, regardless of fever or diarrhea | Oral fluoroquinolone (continue until resolution of neutropenia) |
| Fever with persistent diarrhea, even in the absence of neutropenia | Oral fluoroquinolone (continue until resolution of fever and diarrhea) |

The synthetic octapeptide octreotide has been shown to be effective in the control of diarrhea induced by fluoropyrimidine-based chemotherapy regimens when administered as an escalating dose by continuous infusion or subcutaneous injection. Octreotide can be administered at doses ranging from 100 micrograms twice daily to 500 micrograms three times daily, with a maximum tolerated dose of 2000 micrograms three times daily in a 5-day regimen. Patients should be advised to drink water copiously throughout treatment.

Other Treatments

Symptomatic treatment for other toxicities should be per institutional guidelines. Prevention of alopecia with cold cap or of stomatitis with iced mouth rinses is allowed.

N. Prohibited Therapy

The following drugs are noted in the irinotecan prescribing information as interacting with irinotecan: St. John's Wort, CYP3A4 inducing anticonvulsants (phenytoin, phenobarbital, and carbamazepine), ketoconazole, itraconazole, troleandomycin, erythromycin, diltiazem and verapamil. Treatment with these agents and any other that interact with irinotecan, should be avoided wherever possible. Because 5-FU interacts with warfarin, caution should be exercised if concomitant use is necessary. Refer to the country specific package inserts of 5-FU and leucovorin for any other drug interactions.

The following therapies are not permitted during the trial:
Other anti-neoplastic therapy, including cytotoxics, targeted agents, endocrine therapy or other antibodies;
Potentially curative radiotherapy; palliative radiotherapy is permitted; and
Any other investigational therapy is not permitted.

O. Laboratory Procedures

Complete Blood Count

A complete blood count (CBC) will be performed locally, and must include a white blood count (WBC) and differential, hemoglobin, hematocrit and platelet count.

Serum Chemistry

Serum chemistry panel will be performed centrally. Additionally, chemistry may also be assessed locally, and local lab results may be used for enrollment and treatment decisions, if central lab results are not available. If local lab results are used for enrollment, then local lab results must be used for all subsequent treatment decisions. Serum chemistry will include electrolytes (sodium, potassium, chloride and bicarbonate), BUN, serum creatinine, glucose, direct and total bilirubin, AST, ALT, alkaline phosphatase, LDH, uric acid, total protein, albumin, calcium, magnesium and phosphate.

CA 19-9

CA 19-9 levels will be measured centrally for all patients.

Pregnancy Test

All women of child bearing potential must undergo a urine or serum pregnancy test.

UGT1A1*28 Allele

A whole blood sample will be collected from all patients at baseline and sent to the central lab to test for UGT1A1*28 allele status. Local lab results may be used if the central lab results are not available at the time of randomization.

Pharmacokinetic Assessments

PK analysis will be done centrally. Plasma PK samples will be collected in Cycle 1, from all patients randomized in this study, at the following timepoints:

Arm A: just prior to infusion, during infusion (at 80 to 90 minutes after start of infusion), between 2 and a half and four hours after the start of infusion and on C1D8

Arm B: one sample at the end of 5-FU infusion (C1D2)

Arm C: just prior to MM-398 infusion, during MM-398 infusion (at 80 to 90 minutes after start of infusion), between 2 and a half and four hours after the start of MM-398 infusion, at the end of 5-FU infusion and on C1D8

In addition, a PK sample will be collected in Cycle 1, any time between 8 and 72 hours following administration of MM-398, from patients randomized to Arm A and Arm C, who provide an additional consent for collection of this sample.

P. Pain Assessment and Analgesic Consumption

Pain assessment and analgesic consumption diaries will be provided to the patients for recording their pain intensity daily on a visual analogue scale and to document their daily analgesic use.

Q. EORTC-QLQ-C30

Quality of life will be assessed by the EORTC-QLQ-C30 instrument. The EORTC-QLQ-C30 is a reliable and valid measure of the quality of life of cancer patients in multicultural clinical research settings. It incorporates nine multi-item scales: five functional scales (physical, role, cognitive, emotional, and social); three symptom scales (fatigue, pain, and nausea and vomiting); and a global health and quality-of-life scale. Several single-item symptom measures are also included.

Patients will be required to complete the EORTC-QLQ-C30 questionnaire at timepoints outlined in the Schedule of Assessment. On days that the patient is to receive study drug, assessments should be completed prior to study drug administration. Only those patients, for whom validated translations of the EORTC-QLQ-C30 questionnaire are available, will be required to complete the questionnaire.

R. Overall Survival/Post Study Follow-up

Overall survival data will be collected after a patient completes the 30 day follow-up visit, every 1 month (+/−1 week) from the date of the 30 day follow-up visit. Post-discontinuation data to be collected will include: the date of disease progression (if not already documented; if patient discontinued from study treatment for reasons other than objective disease progression, patient should continue to undergo tumor assessment every 6 weeks, until commencement of new anti-neoplastic therapy or progressive disease); documentation of any anticancer treatment patient has received including the dates of any post-discontinuation systemic therapy, radiotherapy, or surgical intervention; and the date of death. All patients must be followed-up until death or study closure, whichever occurs first.

S. Determining the Severity and Relatedness of Adverse Events

Each adverse event will be graded according to the NCI CTCAE V 4.0, which may be found at http://ctep.cancer.gov/reporting/ctc.html. For events not listed in the CTCAE, severity will be designated as mild, moderate, severe or life threatening or fatal, which correspond to Grades 1, 2, 3, 4 and 5, respectively on the NCI CTCAE, with the following definitions:

Mild: an event not resulting in disability or incapacity and which resolves without intervention;
Moderate: an event not resulting in disability or incapacity but which requires intervention;
Severe: an event resulting in temporary disability or incapacity and which requires intervention;
Life-threatening: an event in which the patient was at risk of death at the time of the event
Fatal: an event that results in the death of the patient The Investigator must attempt to determine if there exists reasonable possibility that an adverse event is related to the use of the study drug. This relationship should be described as related or non-related.

T. Analysis of the Overall Survival

Overall survival (OS) is the primary endpoint of this study. Overall survival is defined as the time from the date of patient randomization to date of death or the date last known alive. For each patient who is not known to have died as of the data-inclusion cut-off date for a particular analysis, OS will be censored for that analysis at the date of last contact prior to the data cut-off date.

The study primary analysis will involve two pair-wise comparisons of survival between the study treatments, in the ITT population using un-stratified Log Rank Test. The testing will be according to the Bonferroni-Holm procedure which strongly controls the family-wise error rate at 0.05 (two-sided) level [25]:

Reject $H_D^1:S_A(t)=S_B(t)$, i.e. no effect of MM-398 monotherapy relative to control, if the log rank p-value for this test is less than 0.025 or if the log rank p-value for this test is less than 0.05 and the log rank p-value for the comparison between Arm B and Arm C is less than 0.025.

Reject $H_D^2:S_C(t)=S_B(t)$, i.e. no effect of MM-398 combination therapy relative to control, if the log rank p-value for this test is less than 0.025 or if the log rank p-value for this test is less than 0.05 and the log rank p-value for the comparison between Arm A and Arm B is less than 0.025.

Kaplan-Meier analyses will be performed on each treatment group to obtain nonparametric estimates of the survival function and the median survival time. Corresponding 95% confidence intervals will be computed using the log-log method. Cox proportional hazards modeling will be used to estimate hazard ratios and corresponding 95% confidence intervals.

The following additional sensitivity analyses will be carried out for overall survival on the ITT population (except as indicated) to evaluate the robustness of the primary analysis results:

log-rank comparisons of treatments on the PP population stratified log rank analyses, using randomization stratification factors [with hazard ratio estimates from stratified Cox modeling]

Wilcoxon comparisons of treatments

Cox regression model with stepwise selection (p value to enter<0.25, p-value to remain <0.15) of model terms where treatment and the prognostic factors (noted below) are candidates for inclusion univariate analyses to evaluate potential independent prognostic factors using Cox regression subgroup analyses to examine differences in the effects of treatment in different segments of the study population.

Repeat all analyses (primary and sensitivity) with only patients who enrolled under protocol Version 2 (and later)

Prognostic factors to be examined include: baseline KPS, baseline albumin, ethnicity, geographic location, disease stage at diagnosis, original tumor location, number of prior chemotherapy treatments, prior radiotherapy, prior surgery, time since last treatment, best response on prior treatment, baseline CA 19-9, gender and age.

U. Secondary Efficacy Analyses

Progression Free Survival

PFS is defined as the number of months from the date of randomization to the date of death or progression, whichever occurred earlier (per RECIST 1.1). If neither death nor progression is observed during the study, PFS data will be censored at the last valid tumor assessment.

PFS will be compared between the treatment groups using paired un-stratified log-rank tests. The PFS curves will be estimated using Kaplan-Meier estimates. Estimates of the hazard ratios and corresponding 95% confidence intervals will be obtained using Cox proportional hazard models. Stratified analyses will also be carried out using the randomization stratification factors. Treatment effects adjusting for stratification variables and other prognostic covariates will be explored. In addition, different censoring and missing data imputing methods may be used to perform sensitivity analyses on PFS. Methodology for the sensitivity analyses will be fully specified in the Statistical Analysis Plan.

The analyses will be performed for ITT, PP and EP populations.

Time to Treatment Failure

Time to treatment failure is defined as time from randomization to either disease progression, death or study discontinuation due to toxicity. Kaplan-Meier analyses as specified for analyses of progression free survival will be performed for time to treatment failure. The analyses will be performed for ITT, PP and EP populations.

Objective Response Rate

The tumor assessment related to ORR will be determined using RECIST v1.1. If the Sponsor requires an independent review of the radiological assessments to support a new drug application or for any other reason, the response status of all patients may be reviewed by an independent panel of clinicians and may be reviewed by the Sponsor or its designee. In case of a discrepancy between the assessment of the independent panel and that of the investigator, the independent panel's assessment will take precedence.

Objective response rate (ORR) for each treatment group will be calculated combining the number of patients with a best overall response of confirmed CR or PR per RECIST. The ORR is the best response recorded from randomization until progression or end of study. The number and percentage of patients experiencing objective response (confirmed CR+PR) at the time of analysis will be presented and the 95% confidence interval for the proportion will be calculated. Objective response rates from the treatment arms will be compared using pair-wise Fisher's Exact Tests. The analyses will be performed for ITT, PP and EP populations.

Tumor Marker Response Analysis

CA 19-9 serum levels will be measured within 7 days before the start of treatment (baseline), and subsequently every 6 weeks. Tumor marker response of CA19-9 will be evaluated by the change of CA19-9 serum levels. Response is defined as a decrease of 50% of CA 19-9 in relation to the baseline level at least once during the treatment period. Only patients with elevated baseline CA 19-9 value (>30 U/mL) will be included in the calculation of tumor marker response rate.

Patient Reported Outcome Analyses

Analysis of the EORTC-QLQ-C30 questionnaires will be performed in accordance with the EORTC guidelines [22].

Safety Analysis

Treatment emergent adverse events will be presented by treatment arm, by patient, by NCI CTCAE grade and by MedDRA system organ class (SOC). Separate listings will be presented for total adverse events, serious adverse events, adverse events related to the study drugs and Grade 3 and 4 adverse events. Laboratory data will be presented by treatment arm and by visit. Abnormal laboratory values will be assessed according to NCI CTCAE grade, where possible. Evaluation of QTc will be done based upon Fridericia's correction method. CTCAE criteria will be applied to the $QTc_F$ (i.e. Grade 3=QTc>500 msec). All the safety analyses will be performed by treatment arm, treatment cycle and week, where appropriate. Overall safety will also be evaluated by grade across cycles, SOC and extent of exposure. Additionally, safety analyses will include a comparison between the treatment arms in all patients in the Safety Population:

Number of blood transfusions required

Proportion of patients requiring G-CSF

Adverse events resulting in dose delay or modification

Pharmacokinetics Analysis

Pharmacokinetic data will be collected on all patients randomized to either of the MM-398 arms. Plasma concentration-time data for MM-398 will be analyzed using population pharmacokinetic methods. Pharmacokinetic parameters will be estimated by Non-Linear Mixed Effects Modeling using NONMEM®, Version 7, Level 1.0 (ICON Development Solutions, Dublin, Ireland). PK parameters will include plasma $C_{max}$, $T_{max}$, AUC (area under the concentration curve), clearance, volume of distribution, and terminal elimination half-life. The effects of patient specific factors (age, race, gender, body weight, hepatic and renal function measures, ECOG value, etc.) on pharmacokinetic parameters will be evaluated. Population PK/PD methods will be used to assess the relationships between drug exposure and efficacy and/or toxicity (e.g. neutropenia, diarrhea) parameters. Additional exploratory analysis may be performed on the PK samples, to help clarify any safety, efficacy or PK issues related to MM-398 that arise during the course of the study. Concentration levels of 5-FU will be summarized descriptively.

Endnotes

While the invention has been described in connection with specific embodiments thereof, it will be understood that it is capable of further modifications and this application is intended to cover any variations, uses, or adaptations of the invention following, in general, the principles of the invention and including such departures from the present disclosure that come within known or customary practice within the art to which the invention pertains and may be applied to the essential features set forth herein. The disclosure of each and every US, international, or other patent or patent application or publication referred to herein is hereby incorporated herein by reference in its entirety.

What is claimed is:

1. A method of treating an exocrine pancreatic cancer, the method comprising intravenously administering an antineoplastic therapy once every two weeks to a human patient having the exocrine pancreatic cancer, the antineoplastic therapy consisting of:
  a. administering a 60-80 mg/m² dose of a liposomal irinotecan composition in a diluted irinotecan injection formulation to the human patient in a single infusion over about 90 minutes, the diluted irinotecan injection formulation comprising irinotecan liposomes in 500 mL of an injectable liquid and a volume of a 5 mg/mL liposomal irinotecan composition effective to deliver the dose of liposomal irinotecan, in combination with
  b. administering a therapeutically effective amount of leucovorin and 5-fluorouracil,
  to treat the exocrine pancreatic cancer in the patient, wherein the irinotecan liposome composition comprises phosphatidylcholine, cholesterol, and a polyethyleneglycol-derivatized phosphatidyl-ethanolamine, and the irinotecan liposomes in the liposomal irinotecan composition have a diameter of approximately 80-140 nm.

2. The method of claim 1, wherein the polyethyleneglycol-derivatized phosphatidyl-ethanolamine is in the amount of approximately one polyethyleneglycol molecule for every 200 phospholipid molecules in the irinotecan liposomes.

3. The method of claim 1, wherein the liposomal irinotecan composition comprises liposomes that are unilamellar lipid bilayer vesicles comprising the phosphatidylcholine and cholesterol, encapsulating irinotecan sucrose octasulfate.

4. The method of claim 1, wherein the exocrine pancreatic cancer has progressed on gemcitabine based therapy prior to the administration of the irinotecan liposome.

5. The method of claim 1, wherein the therapeutically effective amount of leucovorin is 200 mg/m² of the (1) form of leucovorin optionally administered as 400 mg/m² of the (l+d) racemic form of leucovorin, and the therapeutically effective amount of 5-fluorouracil is a 2,400 mg/m² dose.

6. The method of claim 5, wherein the diluted irinotecan injection formulation, leucovorin and 5-fluorouracil are administered sequentially to the patient beginning on day 1 of a 2-week cycle, resulting in the irinotecan liposomes, leucovorin and 5-fluorouracil being simultaneously present in the blood of the patient.

7. The method of claim 6, wherein the diluted irinotecan injection formulation is administered to the patient prior to the 5-fluorouracil.

8. The method of claim 7, wherein:
  a. the patient has previously been treated with gemcitabine;
  b. the leucovorin is administered as 400 mg/m² of the (l+d) racemic form of leucovorin;
  c. the exocrine pancreatic cancer has progressed on gemcitabine based therapy prior to the administration of the diluted irinotecan injection formulation;
  d. the irinotecan liposome composition comprises liposomes that are unilamellar lipid bilayer vesicles comprising phosphatidylcholine and cholesterol, encapsulating irinotecan sucrose octasulfate; and
  e. the irinotecan liposome composition comprises a polyethyleneglycol-derivatized phosphatidyl-ethanolamine in the amount of approximately one polyethyleneglycol molecule for every 200 phospholipid molecules in the irinotecan liposome composition.

9. The method of claim 1, further comprising storing the diluted irinotecan injection formulation at a temperature of about 2-8° C. for no more than 24 hours prior to administration.

10. A method of treating an exocrine pancreatic cancer in a human patient who has previously been treated with gemcitabine, the method comprising intravenously administering to the patient an antineoplastic therapy consisting of:
  a. a 60-80 mg/m² dose of liposomal irinotecan composition comprising irinotecan liposomes in a diluted irinotecan injection formulation, the diluted irinotecan injection formulation obtained by diluting a volume of the liposomal irinotecan composition containing 5 mg/mL of liposomal irinotecan into 500 mL of an injectable liquid, in combination with
  b. a 200 mg/m² dose of the (1) form of leucovorin and a 2,400 mg/m² dose of 5-fluorouracil,
  to treat the exocrine pancreatic cancer in the patient, the irinotecan liposome composition comprising irinotecan sucrose octasulfate encapsulated within the irinotecan composition liposomes comprising phosphatidylcholine, cholesterol, and a polyethyleneglycol-derivatized phosphatidyl-ethanolamine, and having a diameter of approximately 80-140 nm, wherein the diluted irinotecan injection formulation, leucovorin and 5-fluorouracil are administered sequentially to the patient beginning on day 1 of a 2-week cycle.

11. The method of claim 10, further comprising storing the diluted irinotecan injection formulation at a temperature of about 2-8° C. for no more than 24 hours prior to administration.

12. The method of claim 11, wherein the irinotecan liposome composition comprises approximately one polyethyleneglycol (PEG) molecule for every 200 phospholipid molecules.

13. The method of claim 12, wherein the patient has failed prior treatment with gemcitabine or become resistant to gemcitabine prior to administration of the diluted irinotecan injection formulation.

14. The method of claim 13, wherein the 200 mg/m$^2$ dose of the (1) form of leucovorin is provided by administering a 400 mg/m$^2$ dose of the (l+d) form of leucovorin.

15. The method of claim 14, wherein the dose of liposomal irinotecan dose is 60 mg/m$^2$, 70 mg/m$^2$ or 80 mg/m$^2$.

16. The method of claim 15, wherein the dose of liposomal irinotecan dose is 80 mg/m$^2$ and the human patient is not homozygous for the UGT1A1*28 allele.

17. The method of claim 16, wherein the liposomal irinotecan is administered as the diluted irinotecan injection as a 90-minute infusion, the leucovorin is administered after the irinotecan over 30 minutes and the 5-fluorouracil is administered after the leucovorin over 46 hours.

18. The method of claim 17, wherein the irinotecan liposomes are a unilamellar lipid bilayer vesicle that encapsulates an aqueous space which contains irinotecan in a gelated or precipitated state with sucrose octasulfate salt of irinotecan.

19. A method of treating pancreatic cancer in a human patient, whose cancer has progressed following gemcitabine based therapy, the method comprising administering an antineoplastic therapy to the human patient once every two weeks, the antineoplastic therapy consisting of intravenously administering to the human patient: a diluted irinotecan injection formulation providing a 60, 70 or 80 mg/m$^2$ dose of liposomal irinotecan, in combination with a 200 mg/m$^2$ dose of the (1) form of leucovorin and a 2,400 mg/m$^2$ dose of 5-fluorouracil to treat the pancreatic cancer in the human patient, wherein
  a. the liposomes in the diluted irinotecan injection formulation have a diameter of approximately 80-140 nm, and comprise phosphatidylcholine, cholesterol, and a polyethyleneglycol-derivatized phosphatidyl-ethanolamine; and
  b. the diluted irinotecan injection formulation comprises the liposomal irinotecan in 500 mL of an injectable liquid stored at a temperature of about 2-8° C. for no more than 24 hours prior to each administration.

20. The method of claim 19, wherein the diluted irinotecan injection formulation comprises 500 mL of the injectable liquid and a volume of a 5 mg/mL liposomal irinotecan composition, wherein the volume is calculated to deliver the dose of liposomal irinotecan.

21. The method of claim 19, wherein a 80 mg/m$^2$ dose of liposomal irinotecan is administered to a human patient who is not homozygous for the UGT1A1*28 allele; and the 200 mg/m$^2$ dose of the (1) form of leucovorin is provided by administering a 400 mg/m$^2$ dose of the (l+d) form of leucovorin.

22. The method of claim 21, wherein the method further comprises administering an anti-emetic to the patient prior to administering the antineoplastic therapy; and the liposomal irinotecan is administered as the diluted irinotecan injection formulation as a single 90-minute infusion, the leucovorin dose is administered after the liposomal irinotecan over 30 minutes and the 5-fluorouracil dose is administered after the leucovorin over 46 hours.

23. The method of claim 1, wherein the irinotecan liposomes are a unilamellar lipid bilayer vesicle that encapsulates an aqueous space which contains irinotecan in a gelated or precipitated state with sucrose octasulfate salt of irinotecan.

24. The method of claim 23, wherein the injectable liquid is 5% dextrose injection.

25. The method of claim 10, wherein the irinotecan liposomes are a unilamellar lipid bilayer vesicle that encapsulates an aqueous space which contains irinotecan in a gelated or precipitated state with sucrose octasulfate salt of irinotecan.

26. The method of claim 25, wherein the injectable liquid is 5% dextrose injection.

27. The method of claim 19, wherein the irinotecan liposomes are a unilamellar lipid bilayer vesicle that encapsulates an aqueous space which contains irinotecan in a gelated or precipitated state with sucrose octasulfate salt of irinotecan.

28. The method of claim 27, wherein the injectable liquid is 5% dextrose injection.

29. A method of treating metastatic adenocarcinoma of the pancreas after disease progression following gemcitabine-based therapy in a human patient who is not homozygous for the UGT1A1*28 allele, the method comprising the following steps performed once every two weeks:
  a. diluting a volume of a 5 mg/mL liposomal irinotecan composition in 500 mL of an injectable liquid, to obtain a diluted irinotecan injection formulation, then
  b. optionally storing the diluted irinotecan injection formulation at a temperature of about 2-8° C. for no more than 24 hours prior to administration; then
  c. administering an antineoplastic therapy to the human patient, the antineoplastic therapy consisting of intravenously administering to the human patient: the diluted irinotecan injection formulation providing a 80 mg/m$^2$ dose of liposomal irinotecan to the human patient, in combination with a 200 mg/m$^2$ dose of the (1) form of leucovorin and a 2,400 mg/m$^2$ dose of 5-fluorouracil, to treat the pancreatic cancer in the human patient;
  the liposomes in the liposomal irinotecan composition having a diameter of approximately 80-140 nm, and comprising a unilamellar lipid bilayer vesicle that encapsulates an aqueous space which contains irinotecan in a gelated or precipitated state with sucrose octasulfate salt of irinotecan, the unilamellar lipid bilayer comprising phosphatidylcholine, cholesterol, and a polyethyleneglycol-derivatized phosphatidyl-ethanolamine.

30. The method of claim 29, wherein the injectable liquid is 5% dextrose injection.

* * * * *